US012715896B2

(12) United States Patent
Wang et al.

(10) Patent No.: US 12,715,896 B2
(45) Date of Patent: Aug. 25, 2026

(54) SMALL MOLECULE INHIBITORS OF SARS-CoV-2 VIRAL REPLICATION AND USES THEREOF

(71) Applicant: Arizona Board of Regents on Behalf of the University of Arizona, Tucson, AZ (US)

(72) Inventors: Jun Wang, Tucson, AZ (US); Chunlong Ma, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 849 days.

(21) Appl. No.: 17/917,789

(22) PCT Filed: Apr. 7, 2021

(86) PCT No.: PCT/US2021/026253

§ 371 (c)(1),
(2) Date: Oct. 7, 2022

(87) PCT Pub. No.: WO2021/207409

PCT Pub. Date: Oct. 14, 2021

(65) Prior Publication Data

US 2023/0148179 A1 May 11, 2023

Related U.S. Application Data

(60) Provisional application No. 63/007,122, filed on Apr. 8, 2020.

(51) Int. Cl.

| | |
|---|---|
| ***C07K 5/00*** | (2006.01) |
| ***A61K 31/27*** | (2006.01) |
| ***A61K 38/05*** | (2006.01) |
| ***A61K 38/06*** | (2006.01) |
| ***A61K 45/06*** | (2006.01) |
| ***A61P 31/14*** | (2006.01) |
| ***C07C 323/41*** | (2006.01) |
| ***C07K 5/062*** | (2006.01) |
| ***C07K 5/065*** | (2006.01) |
| ***C07K 5/083*** | (2006.01) |
| ***C07K 5/087*** | (2006.01) |

(52) U.S. Cl.

CPC .............. *C07K 5/081* (2013.01); *A61K 31/27* (2013.01); *A61K 38/05* (2013.01); *A61K 38/06* (2013.01); *A61K 45/06* (2013.01); *A61P 31/14* (2018.01); *C07C 323/41* (2013.01); *C07K 5/06034* (2013.01); *C07K 5/0606* (2013.01); *C07K 5/06078* (2013.01); *C07K 5/0808* (2013.01); *C07K 5/0812* (2013.01)

(58) Field of Classification Search

CPC .......... A61K 38/06; A61K 38/00; A61P 31/14
See application file for complete search history.

(56) References Cited

U.S. PATENT DOCUMENTS

| | | | | |
|---|---|---|---|---|
| 5,763,576 | A | 6/1998 | Powers | |
| 8,309,788 | B2 | 11/2012 | Rourke et al. | |
| 2005/0042213 | A1* | 2/2005 | Gelder | A61K 38/57 424/94.64 |
| 2007/0135334 | A1 | 6/2007 | Gazit | |

OTHER PUBLICATIONS

Lee and Goldberg J Biol Chem. vol. 271, No. 44, Issue of November 1, pp. 27280-27284, 1996.*

International Search Report and Written Opinion for PCT/US21/26253. Mailed Nov. 3, 2021. 10 pages.

Cai et al., Conformational plasticity of the 2A proteinase from enterovirus 71. J Virol. Jul. 2013;87(13):7348-56.

Gorbalenya et al., The new scope of virus taxonomy: partitioning the virosphere into 15 hierarchical ranks. Nature Microbiology, 2020, 5, 668-674.

Kim et al., Broad-spectrum antivirals against 3C or 3C-like proteases of picornaviruses, noroviruses, and coronaviruses. J Virol. Nov. 2012;86(21):11754-62.

Kuo et al., Design, synthesis, and evaluation of 3C protease inhibitors as anti-enterovirus 71 agents. Bioorg Med Chem. Aug. 1, 2008;16(15):7388-98.

Lu et al., Genomic characterisation and epidemiology of 2019 novel coronavirus: implications for virus origins and receptor binding. Lancet. Feb. 22, 2020;395(10224):565-574.

Mahase. Coronavirus covid-19 has killed more people than SARS and MERS combined, despite lower case fatality rate. BMJ. Feb. 18, 2020:368:m641. 1 page.

Morrison et al., The behavior and significance of slow-binding enzyme inhibitors. Adv Enzymol Relat Areas Mol Biol. 1988:61:201-301.

Musharrafieh et al., Validating Enterovirus D68-2Apro as an Antiviral Drug Target and the Discovery of Telaprevir as a Potent D68-2Apro Inhibitor. J Virol. Mar. 21, 2019;93(7):e02221-18. 16 pages.

Ono et al., Calpain research for drug discovery: challenges and potential. Nat Rev Drug Discov. Dec. 2016; 15(12):854-876.

Pedersen et al., Efficacy of a 3C-like protease inhibitor in treating various forms of acquired feline infectious peritonitis. J Feline Med Surg. Apr. 2018;20(4):378-392.

(Continued)

*Primary Examiner* — Jeanette M Lieb

(74) *Attorney, Agent, or Firm* — Casimir Jones, S.C.; Robert A. Goetz

(57) ABSTRACT

This invention is in the field of medicinal pharmacology. In particular, the present invention relates to pharmaceutical agents which function as inhibitors of severe acute respiratory syndrome coronavirus 2 (SARS-CoV-2) viral replication and/or SARS-CoV-2 related viral 3CL protease ($M^{pro}$) activity. The invention further relates to methods of treating and/or ameliorating symptoms related to conditions caused by the SARS-CoV-2 virus (e.g., COVID-19), comprising administering to a subject (e.g., a human patient) a composition comprising one or more pharmaceutical agents which function as inhibitors of SARS-CoV-2 viral replication and/or inhibitors of SARS-CoV-2 related $M^{pro}$ activity.

10 Claims, 4 Drawing Sheets

(56) References Cited

OTHER PUBLICATIONS

Pillaiyar et al., An Overview of Severe Acute Respiratory Syndrome-Coronavirus (SARS-CoV) 3CL Protease Inhibitors: Peptidomimetics and Small Molecule Chemotherapy. J Med Chem. Jul. 28, 2016;59(14):6595-628.
Shang et al., Biochemical characterization of recombinant Enterovirus 71 3C protease with fluorogenic model peptide substrates and development of a biochemical assay. Antimicrob Agents Chemother. Apr. 2015;59(4):1827-36.
Shie et al., Inhibition of the severe acute respiratory syndrome 3CL protease by peptidomimetic alpha,beta-unsaturated esters. Bioorg Med Chem. Sep. 1, 2005;13(17):5240-52.
Tang et al., An updated estimation of the risk of transmission of the novel coronavirus (2019-nCov). Infect Dis Model. Feb. 11, 2020:5:248-255.
Wang et al., Remdesivir and chloroquine effectively inhibit the recently emerged novel coronavirus (2019-nCOV) in vitro. Cell Res. Mar. 2020;30(3):269-271.
Wu et al., Genome Composition and Divergence of the Novel Coronavirus (2019-nCOV) Originating in China. Cell Host Microbe. Mar. 11, 2020;27(3):325-328.
Zhang et al., Crystal structure of SARS-CoV-2 main protease provides a basis for design of improved α-ketoamide inhibitors. Science. Apr. 24, 2020;368(6489):409-412.

* cited by examiner

SMALL MOLECULE INHIBITORS OF SARS-CoV-2 VIRAL REPLICATION AND USES THEREOF

CROSS-REFERENCE TO RELATED APPLICATIONS

This application is a Section 371 U.S. national stage entry of International Patent Application No. PCT/US2021/026253, International Filing Date Apr. 7, 2021 which the benefit of U.S. Prov. Appl. 63/007,122 filed Apr. 8, 2020, the entire contents of which are incorporated herein by reference.

STATEMENT REGARDING FEDERALLY SPONSORED RESEARCH OR DEVELOPMENT

This invention was made with government support under Grant No. AI147325 awarded by National Institutes of Health. The government has certain rights in the invention.

FIELD OF THE INVENTION

This invention is in the field of medicinal pharmacology. In particular, the present invention relates to a new class of small-molecules having a formamido-oxoethyl-acetamide (or similar) structure (Formula I)

e.g., 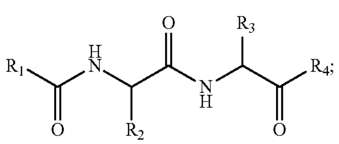

which function as inhibitors of severe acute respiratory syndrome coronavirus 2 (SARS-CoV-2) viral replication and/or SARS-CoV-2 related viral 3CL protease ($M^{pro}$) activity, and which function as therapeutics for the treatment of conditions caused by the SARS-CoV-2 virus (e.g., COVID-19), and which function as therapeutics for the treatment conditions related to SARS-CoV-2 related $M^{pro}$ activity.

INTRODUCTION

An emerging respiratory disease COVID-19 started to circulate among human in December 2019. Since its first outbreak in China from an unknown origin, it quickly became a global pandemic. As of Mar. 13, 2020, there are 4,947 deaths among 132,536 confirmed cases in 123 countries. The etiological pathogen of COVID-19 is a new coronavirus SARS-CoV-2, also called novel coronavirus (nCoV-2019). As the name indicates, SARS-CoV-2 is similar to severe acute respiratory syndrome (SARS), the virus that causes severe respiratory symptoms in human and killed 774 people among 8098 infected worldwide in 2003 (see, Mahase, E., BMJ 2020, 368, m641). SARS-CoV-2 shares ~82% of sequence identity as SARS and to a less extent for Middle East respiratory syndrome (MERS) (~50%) (see, Lu, R.; et al., Lancet 2020, 395 (10224), 565-574; Wu, A.; et al., Cell Host Microbe 2020). SARS-CoV-2 is an enveloped, positive-sense, single-stranded RNA virus that belongs to the β-lineage of the coronavirus (see, Gorbalenya, A. E.; et al., Nature Microbiology 2020), and the β-lineage also contains two other important human pathogens, the SARS coronavirus and MERS coronavirus. The mortality rate of SARS-CoV-2 is around 4.5%, which is lower than that of SARS (~10%) and MERS (~34%) (see, Mahase, E., BMJ 2020, 368, m641). However, current data indicate that SARS-CoV-2 is more contagious and has a larger R0 value than SARS and MERS (see, Tang, B.; et al., Infectious Disease Modelling 2020, 5, 248-255), resulting in higher death tolls than SARS and MERS. The SARS-CoV-2 virus is currently spreading at an alarming speed in Europe and the United States.

Improved treatments for SARS-CoV-2 are desperately needed.

The present invention addresses this need.

SUMMARY

There is currently no antiviral or antiviral for SARS-CoV-2. The SARS-CoV-2 viral genome encodes a number of structural proteins (e.g. capsid spike glycoprotein), non-structural proteins (e.g. 3-chymotrypsin-like protease (3CL or main protease), papain-like protease, helicase, and RNA-dependent RNA polymerase), and accessary proteins. Compounds that target anyone of these viral proteins might be potential antiviral drug candidates.

Experiments conducted during the course of developing embodiments for the present invention focused on the viral 3CL protease, also called the main protease ($M^{pro}$), and aimed to develop potent $M^{pro}$ inhibitors as SAR-CoV-2 antivirals. The SARS-CoV-2 $M^{pro}$ plays an essential role in viral replication by digesting the viral polyproteins at more than 11 sites, and it appears like a high profile target for antiviral drug discovery. The $M^{pro}$ has a unique substrate preference for glutamine at the P1 site (Leu-Gln↓(Ser,Ala, Gly)), a feature that is absent in closely related host proteases, suggesting it is feasible to achieve selectivity by targeting viral $M^{pro}$. As such, such experiments resulted in development of a Fluorescence Resonance Energy Transfer (FRET)-based enzymatic assay for the SARS-CoV-19 $M^{pro}$ and applied it to screen a focused library of protease inhibitors. Such experiments resulted in the identification of several hits targeting SARS-CoV-2 $M^{pro}$ and their mechanism of action. Their in vitro antiviral activity and cellular cytotoxicity was also evaluated against SARS-CoV-2. Overall, these experiments provide a list of drug candidates for SARS-CoV-2 with a confirmed mechanism of action, and the results might help speed up the drug discovery efforts in combating COVID-19. The FRET-based enzymatic assay for the SARS-CoV-19 $M^{pro}$ which was used in a high-throughput screening to identify potent $M^{pro}$ inhibitors. Several novel compounds were identified having a formamido-oxoethyl-acetamide (or similar) structure.

Accordingly, the present invention relates to a new class of small-molecules having a formamido-oxoethyl-acetamide (or similar) structure which function as inhibitors of severe acute respiratory syndrome coronavirus 2 (SARS-CoV-2) viral replication and/or SARS-CoV-2 related viral 3CL protease ($M^{pro}$) activity, and which function as therapeutics for the treatment of conditions caused by the SARS-CoV-2 virus (e.g., COVID-19), and which function as therapeutics for the treatment conditions related to SARS-CoV-2 related $M^{pro}$ activity.

Certain formamido-oxoethyl-acetamide (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within the following formula is provided:

(Formula I)

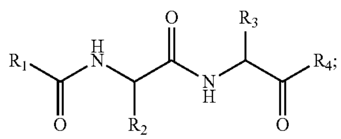

including pharmaceutically acceptable salts, solvates, and/or prodrugs thereof.

Formula I is not limited to a particular chemical moiety for R1, R2, R3, and R4. In some embodiments, the particular chemical moiety for R1, R2, R3, and R4 independently include any chemical moiety that permits the resulting compound to inhibit $M^{pro}$ protease activity. In some embodiments, the particular chemical moiety R1, R2, R3, and R4 independently include any chemical moiety that permits the resulting compound to prevent viral infection (e.g., COVID-19 infection).

Such embodiments are not limited to a particular definition for R1.

In some embodiments, R1 is selected from hydrogen, methyl,

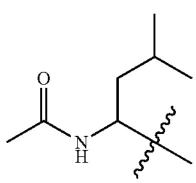
(e.g.,
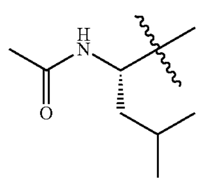
,
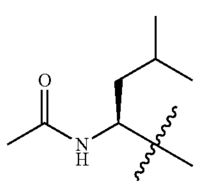
),
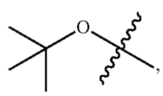
,
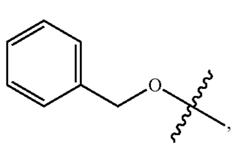
,
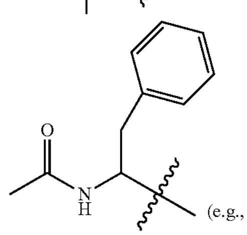
(e.g.,
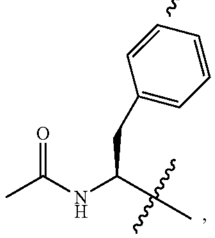
,
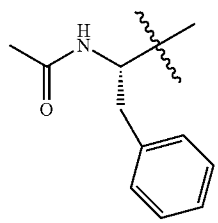
), -continued

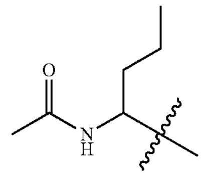
(e.g.,
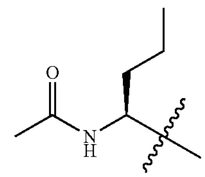
,
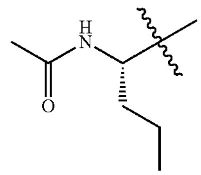
),
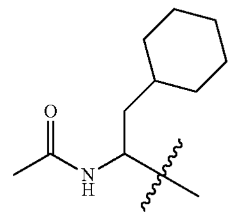
(e.g.,
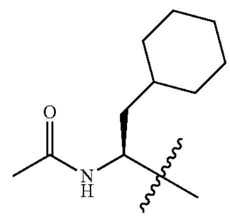
,
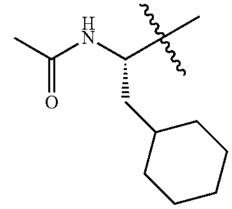
),
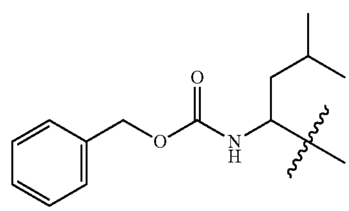
(e.g.,
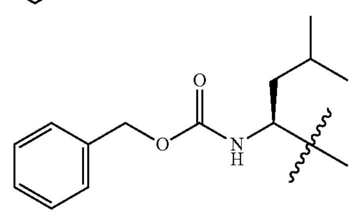
,
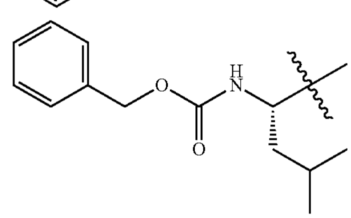
),
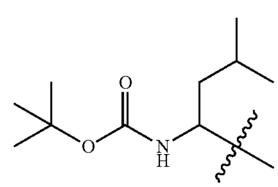
(e.g.,
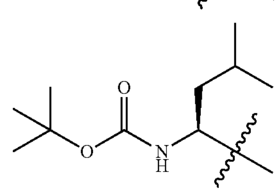
, -continued
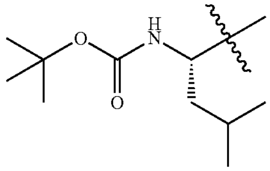
),
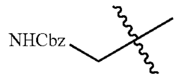
(e.g.,
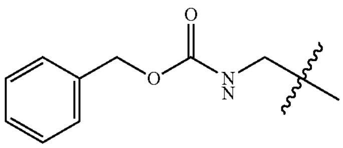
,
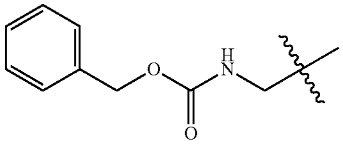
),
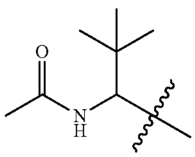
(e.g.,
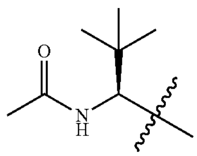
,
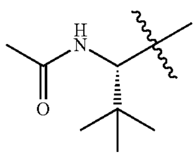
),
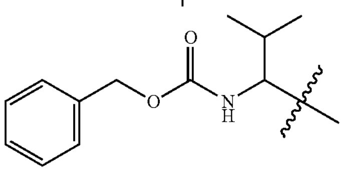
(e.g.,
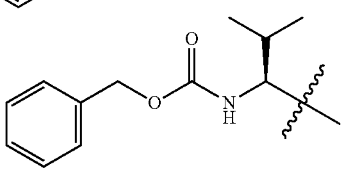
,
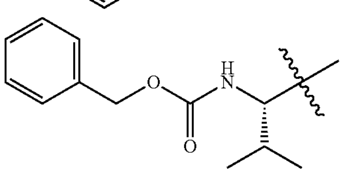
), and
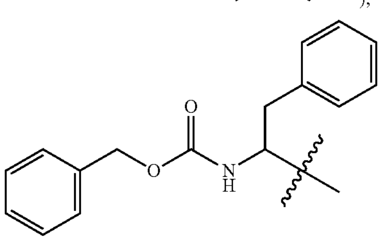
(e.g.,
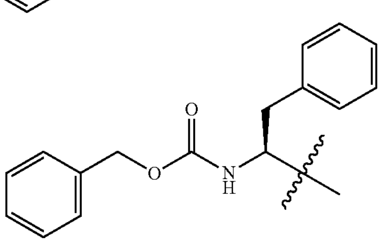
,
-continued
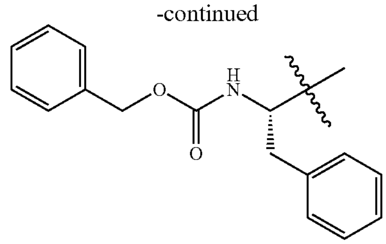
).
Such embodiments are not limited to a particular definition for R2.
In some embodiments, R2 is selected from
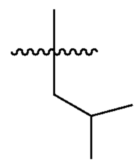
(e.g.,
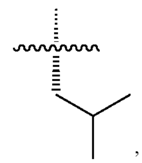
,
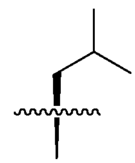
), and
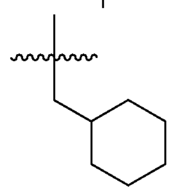
(e.g.,
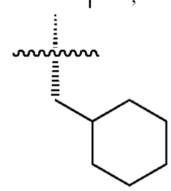
,
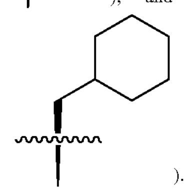
).
Such embodiments are not limited to a particular definition for R3.
In some embodiments, R3 is selected from
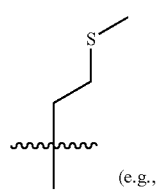
(e.g.,
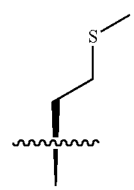
,
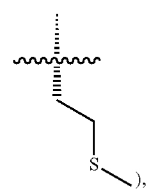
),
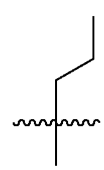
(e.g.,
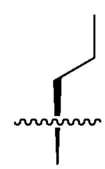
,
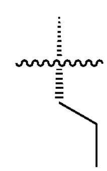
),
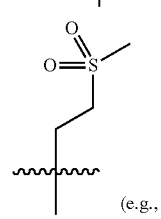
(e.g.,
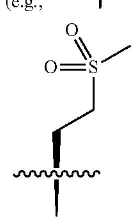
,
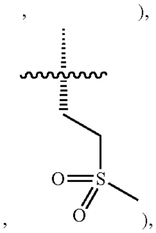
), and
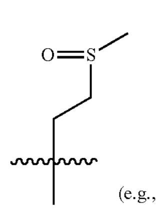
(e.g.,
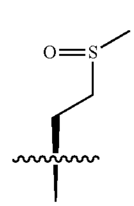
,
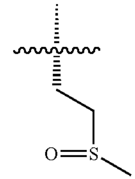
).

Such embodiments are not limited to a particular definition for R4.

In some embodiments, R4 is selected from hydrogen,

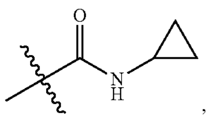
,
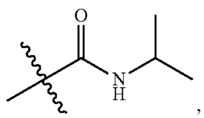
, and
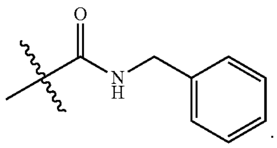
.

In some embodiments, the compound encompassed within Formula I is recited in Table 5 (see, Example I).

The invention further provides processes for preparing any of the compounds of the present invention.

In certain embodiments, the present invention provides compositions comprising a pharmaceutical agent (e.g., comprising one or more compounds of the present invention) capable of inhibiting viral replication (e.g., SARS-CoV-2 viral replication).

In certain embodiments, the present invention provides compositions comprising a pharmaceutical agent (e.g., comprising one or more compounds of the present invention) capable of inhibiting viral 3CL protease ($M^{pro}$) activity (e.g., SARS-CoV-2 related $M^{pro}$ activity).

In certain embodiments, the present invention provides methods for administering a pharmaceutical composition comprising one or more compounds of the present invention to a subject (e.g., a human subject) (e.g., a human subject suffering from or at risk of suffering from a condition related to SARS-CoV-2 infection (e.g., COVID-19)) for purposes of treating, preventing and/or ameliorating the symptoms of a viral infection (e.g., SARS-CoV-2 infection (e.g., COVID-19)).

In such embodiments, the methods are not limited treating, preventing and/or ameliorating the symptoms of a particular type or kind of viral infection. In some embodiments, the viral infection is a SARS-CoV-2 related viral infection (e.g., COVID-19). In some embodiments, the viral infection is any infection related to influenza, HIV, HIV-1, HIV-2, drug-resistant HIV, Junin virus, Chikungunya virus, Yellow Fever virus, Dengue virus, Pichinde virus, Lassa virus, adenovirus, Measles virus, Punta Toro virus, Respiratory Syncytial virus, Rift Valley virus, RHDV, SARS coronavirus, Tacaribe virus, and West Nile virus. In some embodiments, the viral infection is associated with any virus having $M^{pro}$ protease activity and/or expression.

In such embodiments, administration of the pharmaceutical composition results in suppression of $M^{pro}$ protease activity within the subject. In some embodiments, administration of the pharmaceutical composition results in suppression of any pathway related activity related to $M^{pro}$ protease activity within the subject.

In some embodiments, the pharmaceutical composition comprising one or more compounds of the present invention is co-administered with one or more of hydroxychloroquine, dexamethasone, and remdesivir.

In certain embodiments, the present invention provides methods for treating, ameliorating and/or preventing a condition related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the viral infection is a SARS-CoV-2 viral infection.

In certain embodiments, the present invention provides methods for treating, ameliorating and/or preventing SARS-CoV-2 infection (e.g., COVID-19) in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing symptoms related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing symptoms related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing acute respiratory distress syndrome in a subject, comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing acute respiratory distress syndrome related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In some embodiments involving the treatment of acute respiratory distress syndrome and/or pneumonia, the pharmaceutical composition is administered in combination with a known agent to treat respiratory diseases. Known or standard agents or therapies that are used to treat respiratory diseases include, anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisturization by nebulization, anti-tussives, respiratory stimulants, surgery and alpha 1 antitrypsin.

In certain embodiments, the present invention provides methods for inhibiting viral entry in a cell, comprising exposing the cell to a pharmaceutical composition comprising one or more compounds of the present invention. In some embodiments, the cell is at risk of viral infection (e.g., a cell at risk of SARS-CoV-2 infection). In some embodiments, the cell has been exposed to a virus (e.g., a cell currently exposed to SARS-CoV-2). In some embodiments, the cell is in culture. In some embodiments, the cell is a living cell in a subject (e.g., a human subject) (e.g., a human subject suffering from COVID-19) (e.g., a human subject at risk of suffering from COVID-19). In some embodiments, exposure of the cell to the pharmaceutical composition comprising one or more compounds of the present invention results in suppression of $M^{pro}$ activity within the cell.

In certain embodiments, the present invention provides methods for inhibiting viral replication in a cell, comprising exposing the cell a composition comprising a pharmaceutical agent (e.g., comprising one or more compounds of the present invention) capable of inhibiting SARS-CoV-2 viral replication and/or inhibiting SARS-CoV-2 related viral 3CL protease ($M^{pro}$) activity. In some embodiments, the cell is a virus infected cell (e.g., a cell infected with SARS-CoV-2). In some embodiments, the cell is in culture. In some embodiments, the cell is a living cell in a subject (e.g., a human subject) (e.g., a human subject suffering from COVID-19) (e.g., a human subject at risk of suffering from COVID-19). In some embodiments, the viral replication is SARS-CoV-2 viral replication. In some embodiments, the viral replication is reducted by about 50%. In some embodiments, the viral replication is reducted by about 25%. In some embodiments, the viral replication is reducted by about 75%. In some embodiments, the viral replication is reducted by about 99.999%.

In certain embodiments, the present invention provides kits comprising a pharmaceutical composition comprising one or more compounds of the present invention, and one or more of (1) a container, pack, or dispenser, (2) one or more additional agents selected from hydroxychloroquine, dexamethasone, and remdesivir, and (3) instructions for administration.

Such methods are not limited to a particular type or kind of viral infection. In some embodiments, the viral infection is a SARS-CoV-2 related viral infection. In some embodiments, the viral infection is any infection related to influenza, HIV, HIV-1, HIV-2, drug-resistant HIV, Junin virus, Chikungunya virus, Yellow Fever virus, Dengue virus, Pichinde virus, Lassa virus, adenovirus, Measles virus, Punta Toro virus, Respiratory Syncytial virus, Rift Valley virus, RHDV, SARS coronavirus, Tacaribe virus, and West Nile virus. In some embodiments, the viral infection is associated with any virals having $M^{pro}$ protease activity and/or expression.

DETAILED DESCRIPTION OF THE INVENTION

Figure 1:
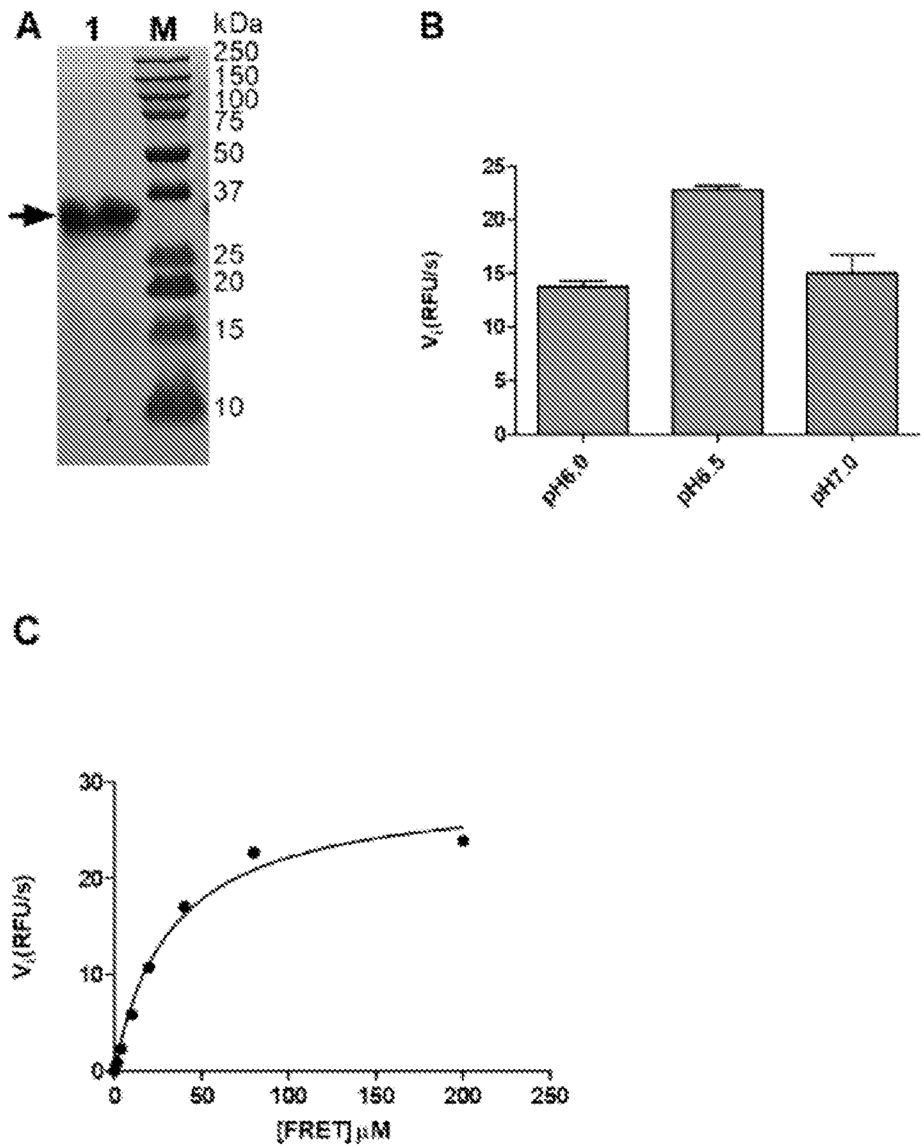
FIG. 1: SARS-CoV-2 $M^{pro}$ expression and characterization. (A) SDS-PAGE of His-tagged-Main protease ($M^{pro}$) (lane 1); Lane M, protein ladder; the calculated molecular weight of the His-tagged-Main protease is 34,992 Da. (B) Reaction buffer optimization: 250 nM His-tagged-$M^{pro}$ was diluted into three reaction buffer with different pH values. (C) Michaelis-Menten plot of 100 nM His-tagged-$M^{pro}$ with the FRET substrate in pH 6.5 reaction buffer.
Figure 2:
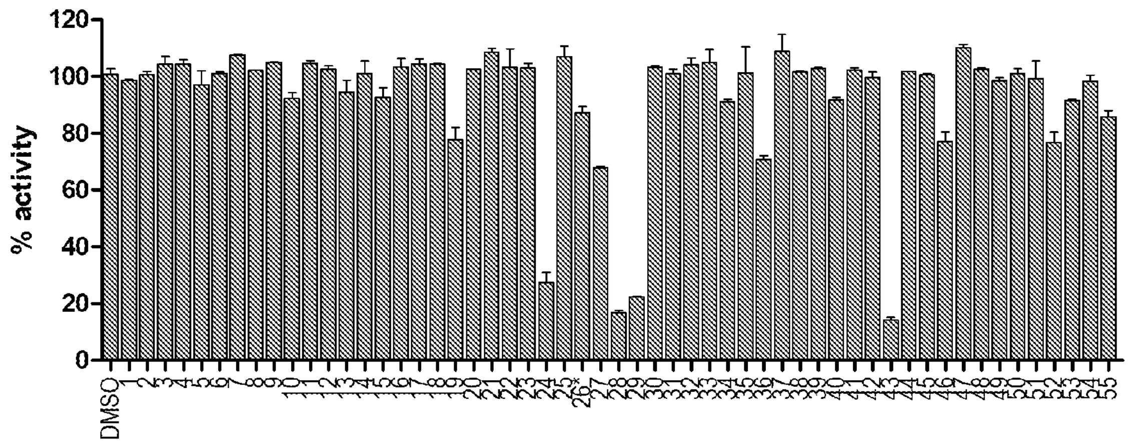
FIG. 2: Screening of the protease inhibitors on SARS-CoV-2 $M^{pro}$ using the FRET assay. 20 μM of compounds (26 was tested at 2 μM) was pre-incubated with 100 nM of SARS-CoV-2 $M^{pro}$ for 30 minutes at 30° C., then 10 μM FRET substrate was added to reaction mixture to initiate the reaction. The reaction was monitored for 2 hours. The initial velocity was calculated by linear regression using the data points from the first 15 minutes of the reaction. The calculated initial velocity with each compound was normalized to DMSO condition.

A novel coronavirus SARS-CoV-2, also called novel coronavirus 2019 (nCoV-19), started to circulate among humans around December 2019, and it is now widespread as a global pandemic. The disease caused by SARS-CoV-2 virus is called COVID-19, which is highly contagious and has an overall mortality rate of 4.5% as of Mar. 26, 2020. There is no vaccine or antiviral available for SARS-CoV-2. Experiments conducted during the course of developing embodiments for the present invention focused on the viral 3CL protease, also called the main protease ($M^{pro}$), and aimed to develop potent $M^{pro}$ inhibitors as SAR-CoV-2 antivirals. The SARS-CoV-2 $M^{pro}$ plays an essential role in viral replication by digesting the viral polyproteins at more than 11 sites, and it appears like a high profile target for antiviral drug discovery. The $M_{pro}$ has a unique substrate preference for glutamine at the P1 site (Leu-Gln↓(Ser,Ala, Gly)), a feature that is absent in closely related host proteases, suggesting it is feasible to achieve selectivity by targeting viral $M^{pro}$. As such, such experiments resulted in development of a Fluorescence Resonance Energy Transfer (FRET)-based enzymatic assay for the SARS-CoV-19 $M^{pro}$ and applied it to screen a focused library of protease inhibitors. Such experiments resulted in the identification of several hits targeting SARS-CoV-2 $M^{pro}$ and their mechanism of action. Their in vitro antiviral activity and cellular cytotoxicity was also evaluated against SARS-CoV-2. Overall, these experiments provide a list of drug candidates for SARS-CoV-2 with a confirmed mechanism of action, and the results might help speed up the drug discovery efforts in combating COVID-19. The FRET-based enzymatic assay for the SARS-CoV-19 $M^{pro}$ which was used in a high-throughput screening to identify potent $M^{pro}$ inhibitors. Several novel compounds were identified having a formamido-oxoethyl-acetamide (or similar) structure.

Accordingly, the present invention relates to a new class of small-molecules having a formamido-oxoethyl-acetamide (or similar) structure which function as inhibitors of severe acute respiratory syndrome coronavirus 2 (SARS-CoV-2) viral replication and/or SARS-CoV-2 related viral 3CL protease ($M^{pro}$) activity, and which function as therapeutics for the treatment of conditions caused by the SARS-CoV-2 virus (e.g., COVID-19), and which function as therapeutics for the treatment conditions related to SARS-CoV-2 related $M^{pro}$ activity.

Certain formamido-oxoethyl-acetamide (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within the following formula is provided:

(Formula I)

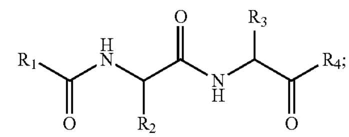

including pharmaceutically acceptable salts, solvates, and/or prodrugs thereof.

Formula I is not limited to a particular chemical moiety for R1, R2, R3, and R4. In some embodiments, the particular chemical moiety for R1, R2, R3, and R4 independently include any chemical moiety that permits the resulting compound to inhibit $M^{pro}$ protease activity. In some embodiments, the particular chemical moiety R1, R2, R3, and R4 independently include any chemical moiety that permits the resulting compound to prevent viral infection (e.g., COVID-19 infection).

Such embodiments are not limited to a particular definition for R1.

In some embodiments, R1 is selected from hydrogen, methyl,

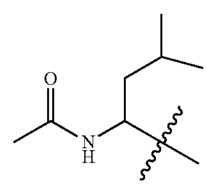 (e.g., 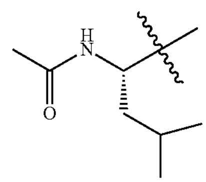, 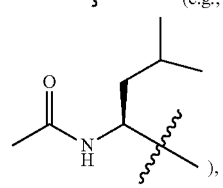), 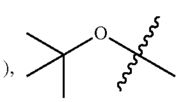, 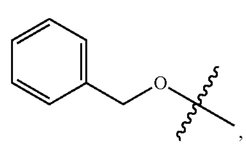, 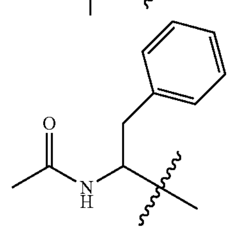 (e.g., 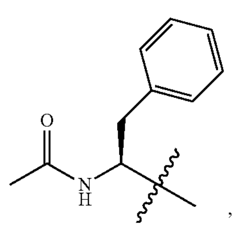, 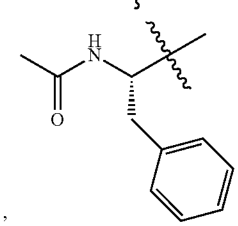), -continued
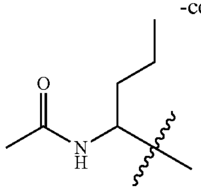
(e.g.,
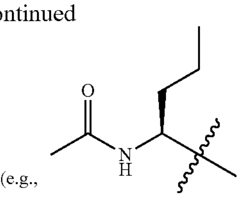
,
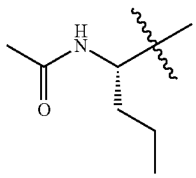
),
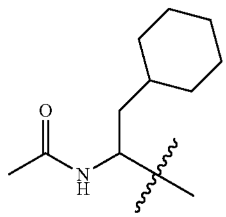
(e.g.,
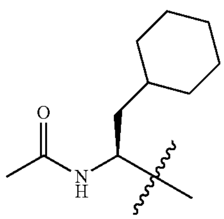
,
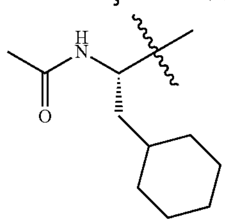
),
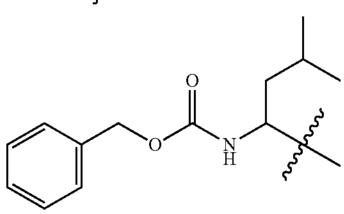
(e.g.,
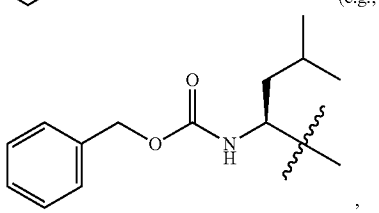
,
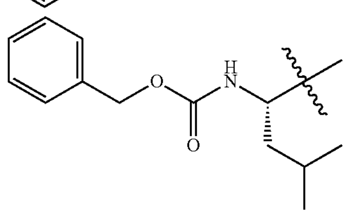
),
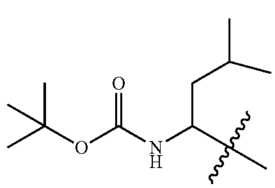
(e.g.,
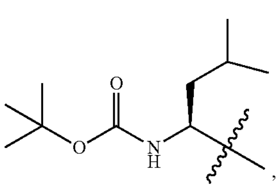
,
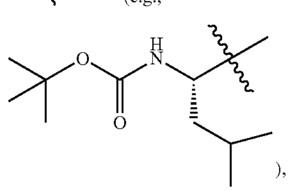
),
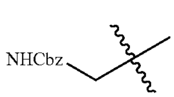
(e.g.,
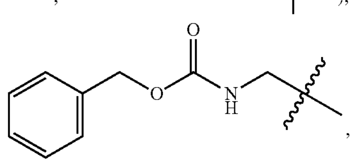
,
-continued
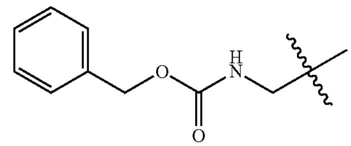
),
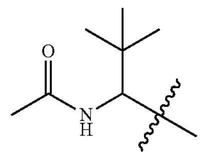
(e.g.,
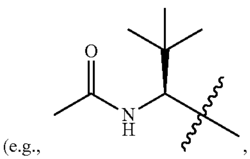
,
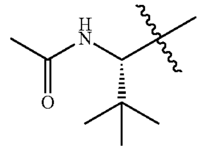
),
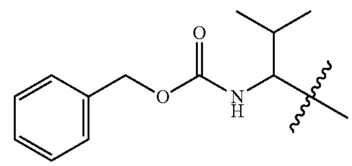
(e.g.,
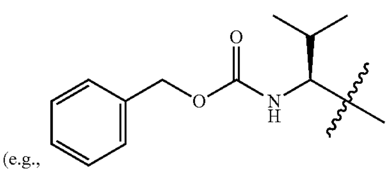
,
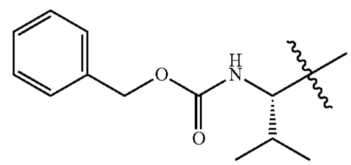
), and
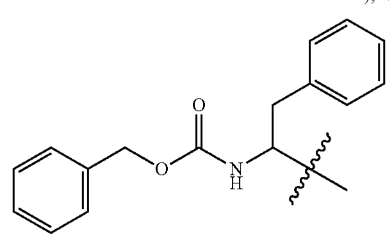
(e.g.,
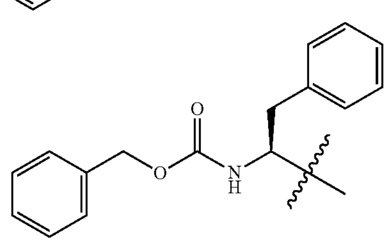
,
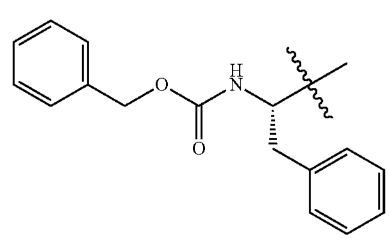
).
Such embodiments are not limited to a particular definition for R2.

In some embodiments, R2 is selected from

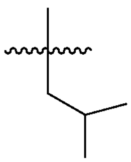 (e.g., 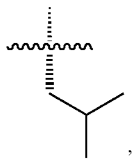, 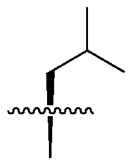), and 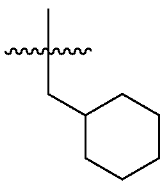 (e.g., 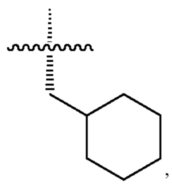, 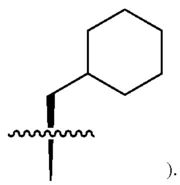).

Such embodiments are not limited to a particular definition for R3.

In some embodiments, R3 is selected from

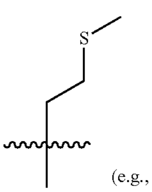 (e.g., 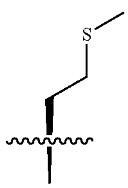, 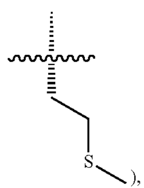), 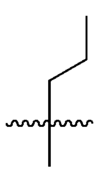 (e.g., 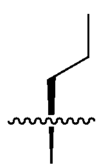, 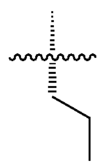), 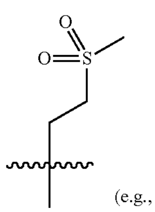 (e.g., 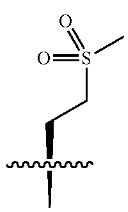, 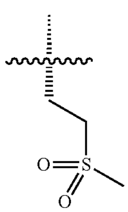), and 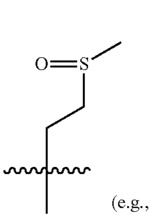 (e.g., 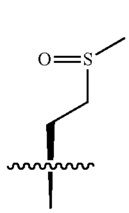, 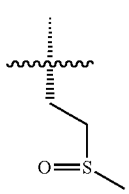).

Such embodiments are not limited to a particular definition for R4.

In some embodiments, R4 is selected from hydrogen,

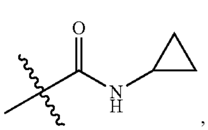, 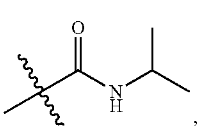, and

-continued

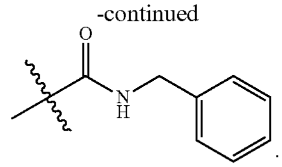.

In some embodiments, the compound encompassed within Formula I is recited in Table 5 (see, Example I).

An important aspect of the present invention is that the pharmaceutical compositions comprising one or more of compounds of the present invention are useful in treating viral infection (e.g., SARS-CoV-2 infection) and symptoms related to such a viral infection (e.g., fever, fatigue, dry cough, myalgias, dyspnea, acute respiratory distress syndrome, and pneumonia).

Some embodiments of the present invention provide methods for administering an effective amount of a pharmaceutical composition comprising one or more compounds of the present invention and at least one additional therapeutic agent (including, but not limited to, any pharmaceutical agent useful in treating SARS-CoV-2 infection and/or symptoms related to such a viral infection (e.g., fever, fatigue, dry cough, myalgias, dyspnea, acute respiratory distress syndrome, and pneumonia). In some embodiments, the additional agent is one or more of hydroxychloroquine, dexamethasone, and remdesivir.

In certain embodiments, the present invention provides methods for administering a pharmaceutical composition comprising one or more compounds of the present invention to a subject (e.g., a human subject) (e.g., a human subject suffering from or at risk of suffering from a condition related to SARS-CoV-2 infection (e.g., COVID-19)) for purposes of treating, preventing and/or ameliorating the symptoms of a viral infection (e.g., SARS-CoV-2 infection (e.g., COVID-19)).

In such embodiments, the methods are not limited treating, preventing and/or ameliorating the symptoms of a particular type or kind of viral infection. In some embodiments, the viral infection is a SARS-CoV-2 related viral infection (e.g., COVID-19). In some embodiments, the viral infection is any infection related to influenza, HIV, HIV-1, HIV-2, drug-resistant HIV, Junin virus, Chikungunya virus, Yellow Fever virus, Dengue virus, Pichinde virus, Lassa virus, adenovirus, Measles virus, Punta Toro virus, Respiratory Syncytial virus, Rift Valley virus, RHDV, SARS coronavirus, Tacaribe virus, and West Nile virus. In some embodiments, the viral infection is associated with any virus having $M^{pro}$ protease activity and/or expression.

In such embodiments, administration of the pharmaceutical composition results in suppression of $M^{pro}$ protease activity within the subject. In some embodiments, administration of the pharmaceutical composition results in suppression of any pathway related activity related to $M^{pro}$ protease activity within the subject.

In some embodiments, the pharmaceutical composition comprising one or more compounds of the present invention is co-administered with one or more of hydroxychloroquine, dexamethasone, and remdesivir.

In certain embodiments, the present invention provides methods for treating, ameliorating and/or preventing a condition related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the viral infection is a SARS-CoV-2 viral infection.

In certain embodiments, the present invention provides methods for treating, ameliorating and/or preventing SARS-CoV-2 infection (e.g., COVID-19) in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing symptoms related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing symptoms related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing acute respiratory distress syndrome in a subject, comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing acute respiratory distress syndrome related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In some embodiments involving the treatment of acute respiratory distress syndrome and/or pneumonia, the pharmaceutical composition is administered in combination with a known agent to treat respiratory diseases. Known or standard agents or therapies that are used to treat respiratory diseases include, anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisturization by nebulization, anti-tussives, respiratory stimulants, surgery and alpha 1 antitrypsin.

In certain embodiments, the present invention provides methods for inhibiting viral entry in a cell, comprising exposing the cell to a pharmaceutical composition comprising one or more compounds of the present invention. In some embodiments, the cell is at risk of viral infection (e.g., a cell at risk of SARS-CoV-2 infection). In some embodiments, the cell has been exposed to a virus (e.g., a cell currently exposed to SARS-CoV-2). In some embodiments, the cell is in culture. In some embodiments, the cell is a living cell in a subject (e.g., a human subject) (e.g., a human subject suffering from COVID-19) (e.g., a human subject at risk of suffering from COVID-19). In some embodiments, exposure of the cell to the pharmaceutical composition comprising one or more compounds of the present invention results in suppression of $M^{pro}$ activity within the cell.

In certain embodiments, the present invention provides kits comprising a pharmaceutical composition comprising one or more compounds of the present invention, and one or more of (1) a container, pack, or dispenser, (2) one or more additional agents selected from hydroxychloroquine, dexamethasone, and remdesivir, and (3) instructions for administration.

Compositions within the scope of this invention include all pharmaceutical compositions contained in an amount that is effective to achieve its intended purpose. While individual needs vary, determination of optimal ranges of effective amounts of each component is within the skill of the art. Typically, the pharmaceutical agents which function as inhibitors of $M^{pro}$ protease activity may be administered to mammals, e.g. humans, orally at a dose of 0.0025 to 50 mg/kg, or an equivalent amount of the pharmaceutically acceptable salt thereof, per day of the body weight of the mammal being treated. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the inhibiting agent. The unit dose may be administered one or more times daily as one or more tablets or capsules each containing from about 0.1 to about 10 mg, conveniently about 0.25 to 50 mg of the agent (e.g., small molecule) or its solvates.

In a topical formulation, a compound of the present invention (e.g., a compound having a methyl-acetamido-propanamide structure) may be present at a concentration of about 0.01 to 100 mg per gram of carrier. In a one embodiment, such a compound is present at a concentration of about 0.07-1.0 mg/ml, for example, about 0.1-0.5 mg/ml, and in one embodiment, about 0.4 mg/ml.

In addition to administering a compound of the present invention (e.g., a compound having a methyl-acetamido-propanamide structure) as a raw chemical, it may be administered as part of a pharmaceutical preparation containing suitable pharmaceutically acceptable carriers comprising excipients and auxiliaries which facilitate processing of the compound into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active mimetic peptide(s), together with the excipient.

The pharmaceutical compositions of the invention may be administered to any patient that may experience the beneficial effects of one or more of compounds of the present invention (e.g., compounds having a methyl-acetamido-propanamide structure). Foremost among such patients are mammals, e.g., humans, although the invention is not intended to be so limited. Other patients include veterinary animals (cows, sheep, pigs, horses, dogs, cats and the like).

The pharmaceutical compositions comprising a compound of the present invention (e.g., a compound having a methyl-acetamido-propanamide structure) may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active mimetic peptides with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye-stuffs or pigments may be added to the tablets or dragee coatings, for example, for identification or in order to characterize combinations of active mimetic peptide doses.

Other pharmaceutical preparations that can be used orally include push-fit capsules made of gelatin, as well as soft, sealed capsules made of gelatin and a plasticizer such as glycerol or sorbitol. The push-fit capsules can contain the active mimetic peptides in the form of granules that may be mixed with fillers such as lactose, binders such as starches, and/or lubricants such as talc or magnesium stearate and, optionally, stabilizers. In soft capsules, the active mimetic peptides are in one embodiment dissolved or suspended in suitable liquids, such as fatty oils, or liquid paraffin. In addition, stabilizers may be added.

Possible pharmaceutical preparations that can be used rectally include, for example, suppositories, which consist of a combination of one or more of the active mimetic peptides with a suppository base. Suitable suppository bases are, for example, natural or synthetic triglycerides, or paraffin hydrocarbons. In addition, it is also possible to use gelatin rectal capsules that consist of a combination of the active mimetic peptides with a base. Possible base materials include, for example, liquid triglycerides, polyethylene glycols, or paraffin hydrocarbons.

Suitable formulations for parenteral administration include aqueous solutions of the active mimetic peptides in water-soluble form, for example, water-soluble salts and alkaline solutions. In addition, suspensions of the active mimetic peptides as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one that includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

EXPERIMENTAL

Example I

Establishing the FRET-Based Assay for the SARS-CoV-2 Main Protease ($M^{pro}$)

The $M^{pro}$ gene from SARS-CoV-2 strain BetaCoV/Wuhan/WIV04/2019 was inserted into pET-29a(+) vector and expressed in BL21(DE3) *E. coli.* with a His-tag in its C-terminus. The $M^{pro}$ protein was purified with Ni-NTA column to high purity (FIG. 1A). To establish the FRET assay condition, we designed a FRET based substrate using the sequence between viral polypeptide NSP4-NSP5 junction from SARS-CoV-2: Dabcyl-KTSAVLQ/SGFRKME (Edans). We then tested the $M^{pro}$ proteolytic activity in different pH. We found that $M^{pro}$ displays highest activity in pH 6.5 buffer (FIG. 1B), which contains 20 mM HEPES, 120 mM NaCl, 0.4 mM EDTA, and 4 mM DTT and 20% glycerol. As such, all the following proteolytic assay was conducted in this pH 6.5 buffer. Next, we characterized the enzymatic activity of this SARS-CoV-2 $M^{pro}$ by measuring the $K_m$ and $V_{max}$ values. When 100 nM $M^{pro}$ was mixed with various concentration of FRET substrate (0 to 200 μM), the initial velocity was measured and plotted against substrate concentration. Curve fitting with Michealis-Menton equation gave the best-fit values for $K_m$ and $V_{max}$ as 32.8±3.5 μM and 29.4±1.1 RFU/s, respectively (FIG. 1C).

The reported kcat/Km value for SARS-CoV-2 3CLP" is 3426.1±416.9 $s^{-1}M^{-1}$ (see, Zhang, L.; et al., Crystal structure of SARS-CoV-2 main protease provides a basis for design of improved alpha-ketoamide inhibitors. Science 2020).

Primary Screening of a Focused Protease Library Against the SARS-CoV-2 $M^{pro}$ With the established FRET assay condition, we screened a collection of protease inhibitors from the Selleckchem bioactive compound library to identify potential SARS-CoV-2 $M^{pro}$ inhibitors. The protease inhibitors are grouped based on their targets and mechanism of action and include proteasome inhibitors (1-8); HIV protease inhibitors (9-14); γ-secretase inhibitors (15-22); HCV NS3-4A protease inhibitors (23-29); DPP-4 inhibitors (30-35); miscellaneous serine protease inhibitors (36-39); cathepsin and calpain protease inhibitors (40-43); miscellaneous cysteine protease inhibitors (44-48); matrix metalloprotease inhibitors (49-51); and miscellaneous protease inhibitors (52-55). The inhibitors were pre-incubated with 100 nM of $M^{pro}$ at 30° C. for 30 min before the addition of 10 μM FRET substrate. All compounds were tested at 20 μM, except compound 26, which was tested at 2 μM due to its fluorescent background. Encouragingly, four inhibitors (24, 28, 29 and 43) show more than 60% inhibition against $M^{pro}$ at 20 μM. Among the hits, simeprevir (24), boceprevir (28), and narlaprevir (29) are HCV NS3-4A serine protease inhibitors, and compound MG-132 (43) is a known inhibitor for both proteasome and calpain.

TABLE 1
| List of protease inhibitors tested against SARS-CoV-2 Mpro. |
|---|
| Proteosome inhibitors |
| 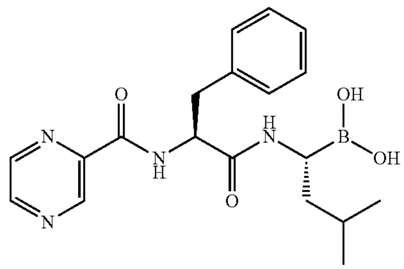 [SMILES: CC(C)C[C@H](NC(=O)[C@H](Cc1ccccc1)NC(=O)c1cnccn1)B(O)O] |
| Bortezomib (PS-341) (1) |
| 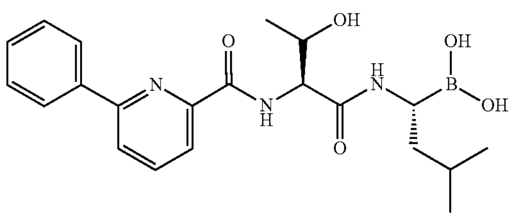 [SMILES: CC(C)C[C@H](NC(=O)[C@@H](NC(=O)c1cccc(-c2ccccc2)n1)C(C)O)B(O)O] |
| CEP-18770 (Delanzomib) (2) |
| 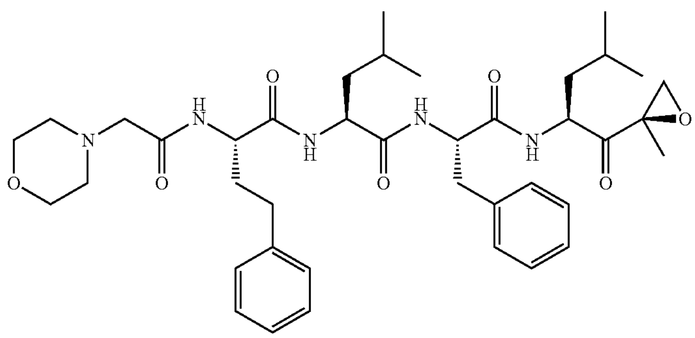 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1] |
| Carfilzomib (PR-171) (3) |
| 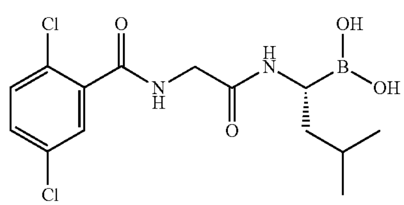 [SMILES: CC(C)C[C@H](NC(=O)CNC(=O)c1cc(Cl)ccc1Cl)B(O)O] |
| MLN2238 (4) |
| 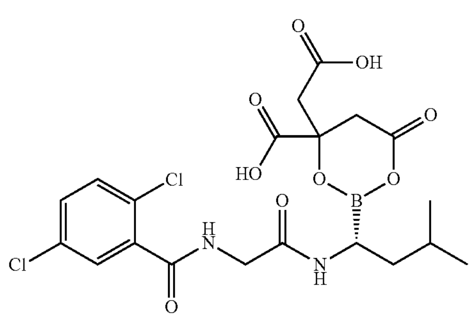 [SMILES: CC(C)C[C@H](NC(=O)CNC(=O)c1cc(Cl)ccc1Cl)B1OC(=O)CC(CC(=O)O)(C(=O)O)O1] |
| MLN9708 (5) |

TABLE 1-continued
List of protease inhibitors tested against SARS-CoV-2 Mpro.
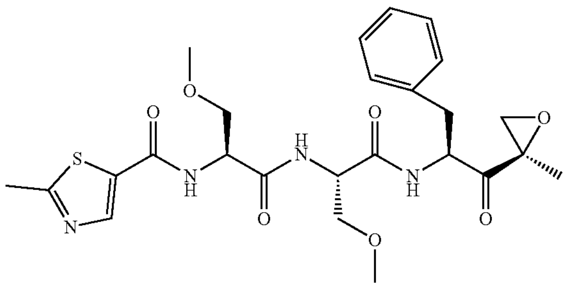
Oprozomib (ONX 0912) (6)
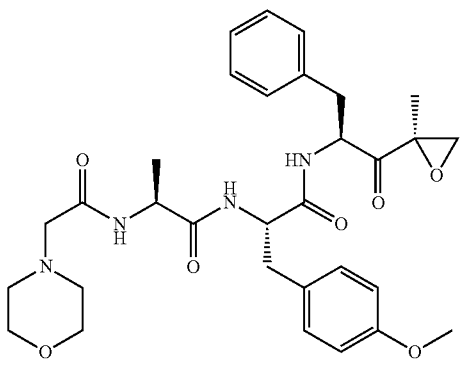 [SMILES: COc1ccc(C[C@H](NC(=O)[C@H](C)NC(=O)CN2CCOCC2)C(=O)N[C@@H](Cc2ccccc2)C(=O)[C@@]2(C)CO2)cc1]
ONX-0914 (PR-957) (7)
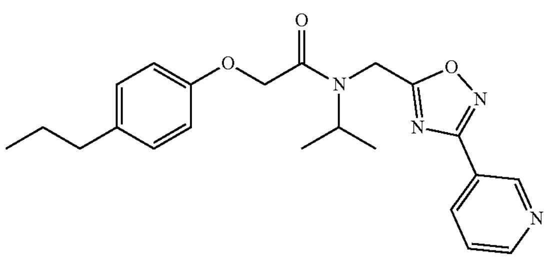 [SMILES: CCCc1ccc(OCC(=O)N(Cc2nc(-c3cccnc3)no2)C(C)C)cc1]
PI-1840 (8)
HIV protease (aspartic protease) inhibitors
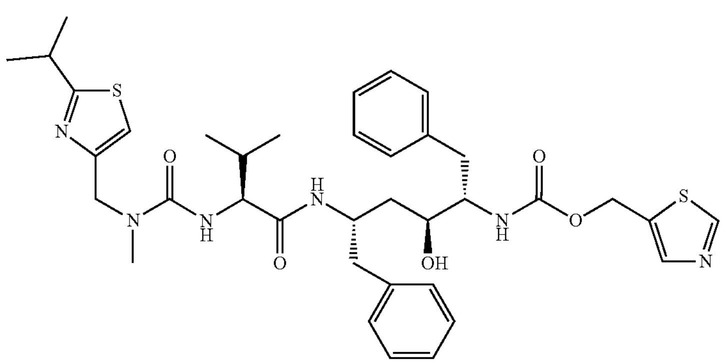 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1]
Ritonavir (9)

TABLE 1-continued
| List of protease inhibitors tested against SARS-CoV-2 Mpro. |
| --- |
| 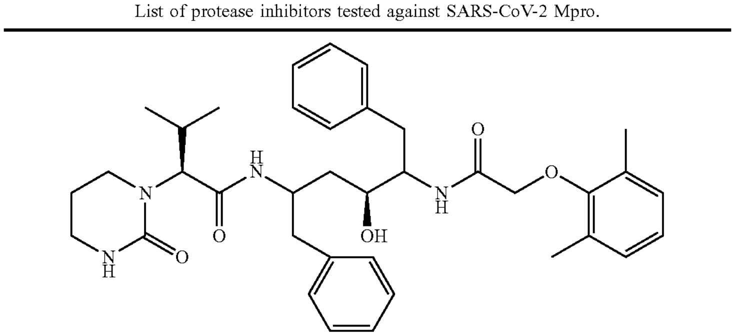<br>Lopinavir (10) |
| 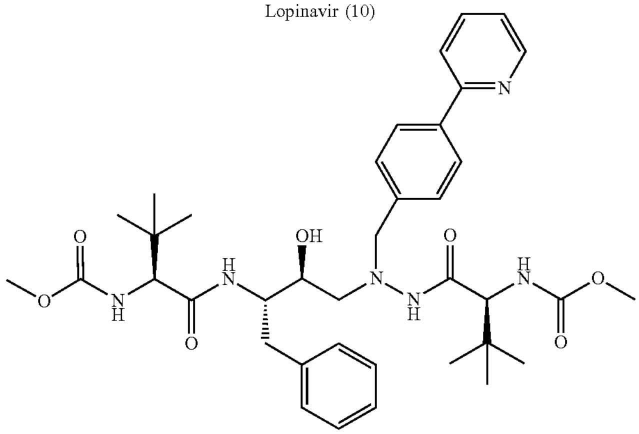<br>Atazanavir (11) |
| 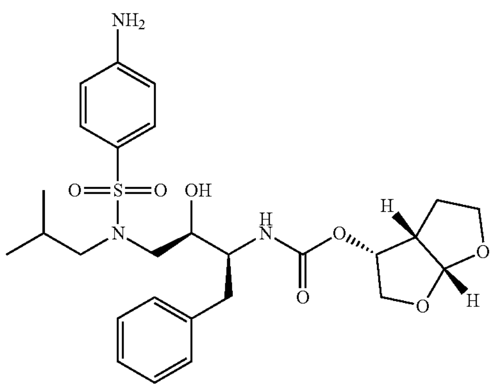 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]<br>Darunavir (12) |
| 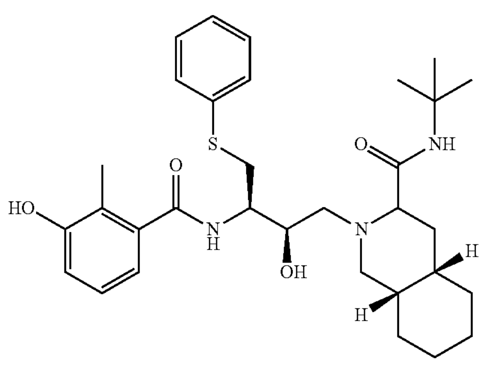 [SMILES: Cc1c(O)cccc1C(=O)N[C@@H](CSc1ccccc1)[C@H](O)CN1C[C@H]2CCCC[C@H]2CC1C(=O)NC(C)(C)C]<br>Nelfinavir (13) |

TABLE 1-continued
| List of protease inhibitors tested against SARS-CoV-2 Mpro. |
| --- |
| 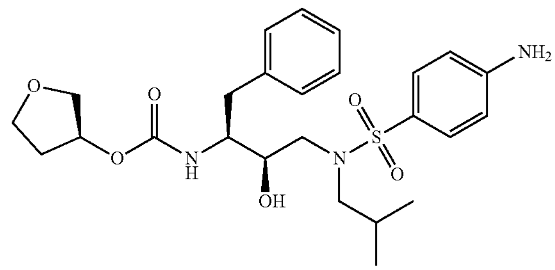 [SMILES: CC(C)CN(C[C@@H](O)[C@H](Cc1ccccc1)NC(=O)O[C@H]1CCOC1)S(=O)(=O)c1ccc(N)cc1]<br>Amprenavir (14) |
| γ-secretase (aspartic protease) inhibitors |
| 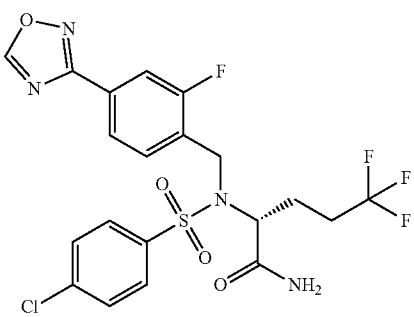 [SMILES: NC(=O)[C@@H](CCC(F)(F)F)N(Cc1ccc(-c2ncon2)cc1F)S(=O)(=O)c1ccc(Cl)cc1]<br>Avagacestat (15) |
| 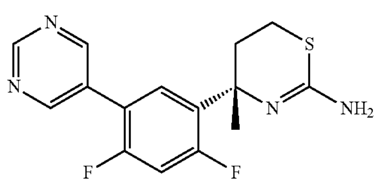 [SMILES: C[C@@]1(c2cc(-c3cncnc3)c(F)cc2F)CCSC(N)=N1]<br>LY2811376 (16) |
| 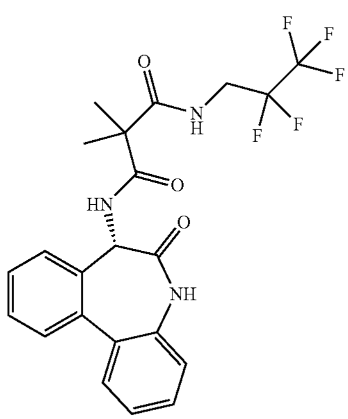 [SMILES: CC(C)(C(=O)NCC(F)(F)C(F)(F)F)C(=O)N[C@@H]1C(=O)Nc2ccccc2-c2ccccc21]<br>RO4929097 (17) |

TABLE 1-continued
| List of protease inhibitors tested against SARS-CoV-2 Mpro. |
| --- |
| 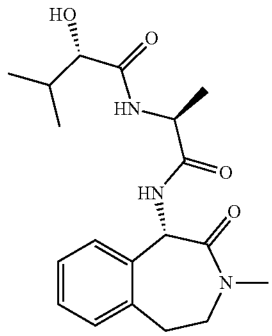 [SMILES: CC(C)[C@H](O)C(=O)N[C@@H](C)C(=O)N[C@@H]1C(=O)N(C)CCc2ccccc21] |
| Semagacestat (LY450139) (18) |
| 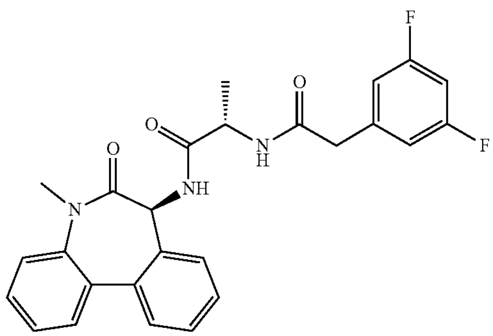 [SMILES: C[C@H](NC(=O)Cc1cc(F)cc(F)c1)C(=O)N[C@@H]1C(=O)N(C)c2ccccc2-c2ccccc21] |
| YO-01027(19) |
| 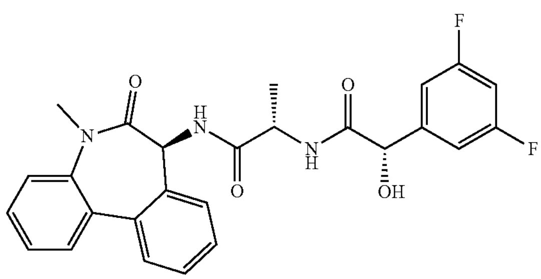 [SMILES: C[C@H](NC(=O)[C@@H](O)c1cc(F)cc(F)c1)C(=O)N[C@@H]1C(=O)N(C)c2ccccc2-c2ccccc21] |
| LY411575 (20) |
| 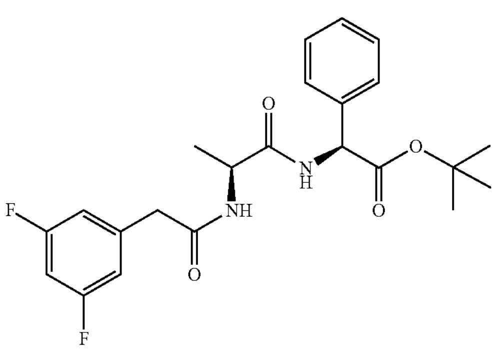 [SMILES: C[C@H](NC(=O)Cc1cc(F)cc(F)c1)C(=O)N[C@H](C(=O)OC(C)(C)C)c1ccccc1] |
| DAPT (GSI-IX) (21) |

TABLE 1-continued
| List of protease inhibitors tested against SARS-CoV-2 Mpro. |
|---|
| 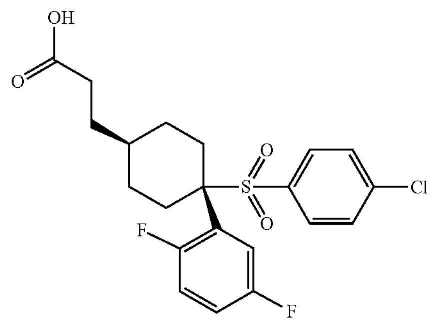 [SMILES: O=C(O)CC[C@H]1CC[C@](c2cc(F)ccc2F)(S(=O)(=O)c2ccc(Cl)cc2)CC1] |
| MK-0752 (22) |
| HCV protease (serine protease) inhibitors |
| 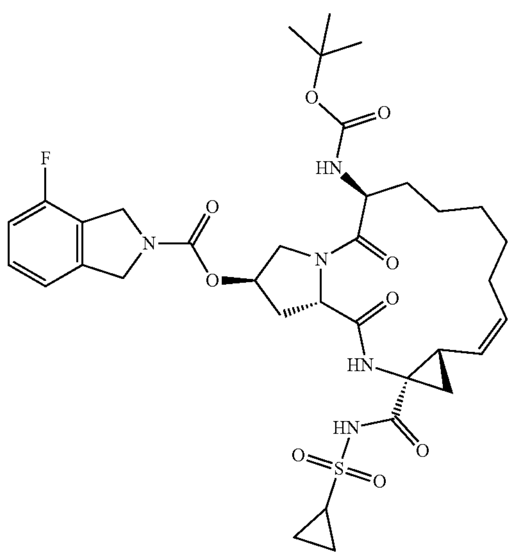 [SMILES: CC(C)(C)OC(=O)N[C@H]1CCCCC/C=C\[C@@H]2C[C@@]2(C(=O)NS(=O)(=O)C2CC2)NC(=O)[C@@H]2C[C@@H](OC(=O)N3Cc4cccc(F)c4C3)CN2C1=O] |
| Danoprevir (23) |
| 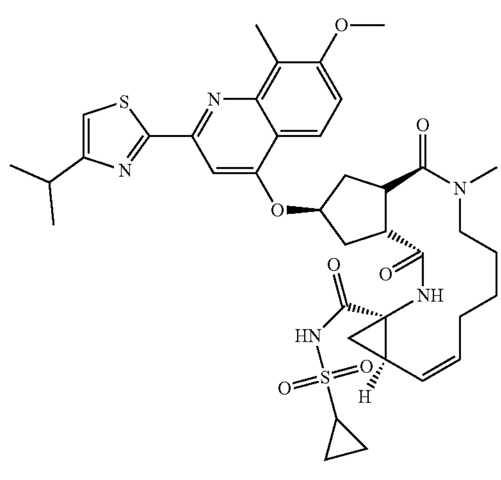 |
| Simeprevir (24) |

TABLE 1-continued
| List of protease inhibitors tested against SARS-CoV-2 Mpro. |
|---|
| 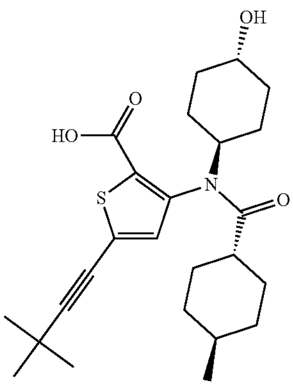 [SMILES: CC(C)(C)C#Cc1cc(N(C(=O)[C@H]2CC[C@H](C)CC2)[C@H]2CC[C@H](O)CC2)c(C(=O)O)s1] |
| Lomibuvir (VX-222) (25) |
| 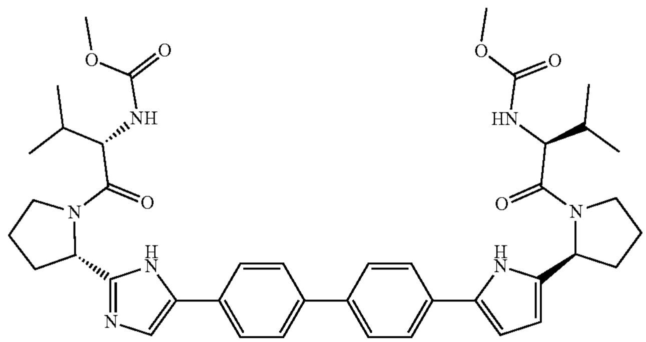 [SMILES: COC(=O)N[C@H](C(=O)N1CCC[C@H]1c1ccc(-c2ccc(-c3ccc(-c4cnc([C@@H]5CCCN5C(=O)[C@@H](NC(=O)OC)C(C)C)[nH]4)cc3)cc2)[nH]1)C(C)C] |
| Daclatasvir (BMS-790052 (26) |
| 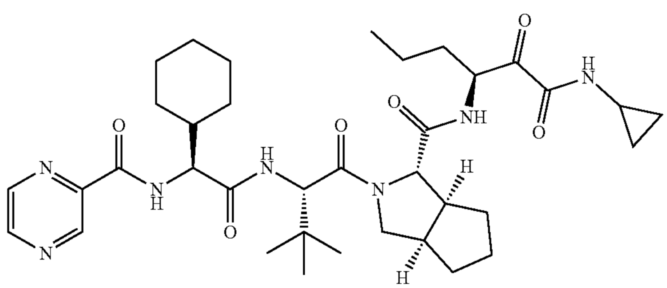 [SMILES: CCC[C@H](NC(=O)[C@@H]1[C@H]2CCC[C@H]2CN1C(=O)[C@@H](NC(=O)[C@@H](NC(=O)c1cnccn1)C1CCCCC1)C(C)(C)C)C(=O)C(=O)NC1CC1] |
| Telaprevir (27) |
| 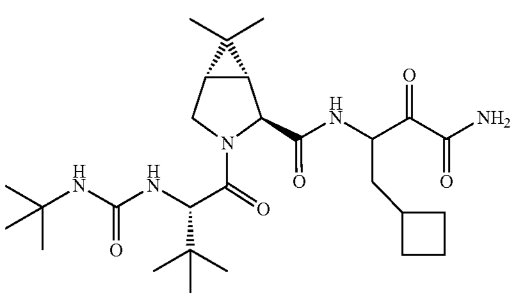 [SMILES: CC(C)(C)NC(=O)N[C@H](C(=O)N1C[C@H]2[C@@H]([C@H]1C(=O)NC(CC1CCC1)C(=O)C(N)=O)C2(C)C)C(C)(C)C] |
| Boceprevir (28) |

TABLE 1-continued
| List of protease inhibitors tested against SARS-CoV-2 Mpro. |
|---|
| 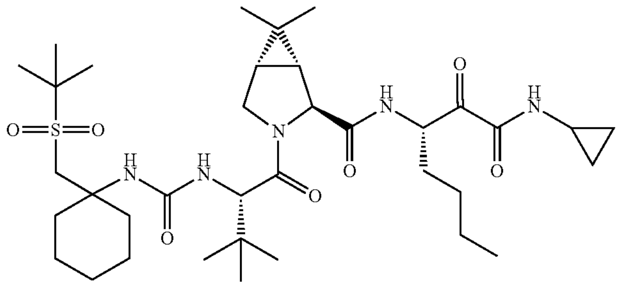 [SMILES: CCCC[C@H](NC(=O)[C@@H]1[C@@H]2[C@H](CN1C(=O)[C@@H](NC(=O)NC1(CS(=O)(=O)C(C)(C)C)CCCCC1)C(C)(C)C)C2(C)C)C(=O)C(=O)NC1CC1] |
| Narlaprevir (29) |
| DPP-4 (serine protease) inhibitors |
| 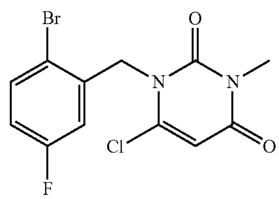 [SMILES: Cn1c(=O)cc(Cl)n(Cc2cc(F)ccc2Br)c1=O] |
| Trelagliptin (30) |
| 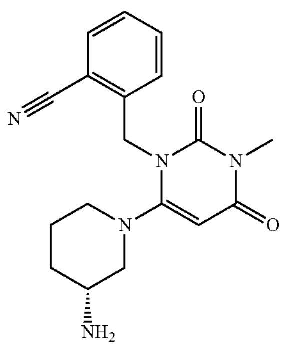 [SMILES: Cn1c(=O)cc(N2CCC[C@@H](N)C2)n(Cc2ccccc2C#N)c1=O] |
| Alogliptin (31) |
| 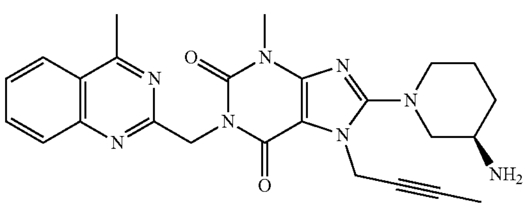 [SMILES: CC#CCn1c(N2CCC[C@@H](N)C2)nc2c1c(=O)n(Cc1nc(C)c3ccccc3n1)c(=O)n2C] |
| Linagliptin (32) |
| 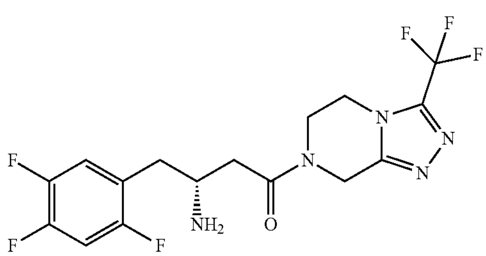 [SMILES: N[C@@H](CC(=O)N1CCn2c(nnc2C(F)(F)F)C1)Cc1cc(F)c(F)cc1F] |
| Sitagliptin (33) |

TABLE 1-continued
| List of protease inhibitors tested against SARS-CoV-2 Mpro. |
| --- |
| 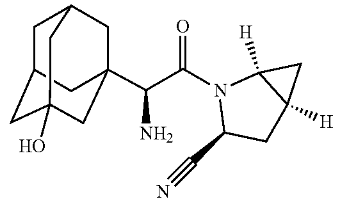 [SMILES: N#C[C@@H]1C[C@@H]2C[C@@H]2N1C(=O)[C@@H](N)C12CC3CC(CC(O)(C3)C1)C2] |
| Saxagliptin (34) |
| 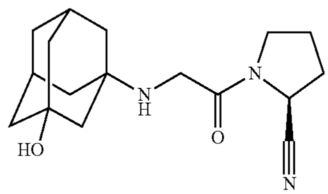 [SMILES: N#C[C@@H]1CCCN1C(=O)CNC12CC3CC(CC(O)(C3)C1)C2] |
| Vildagliptin (35) |
| Miscellaneous serine protease inhibitors |
| 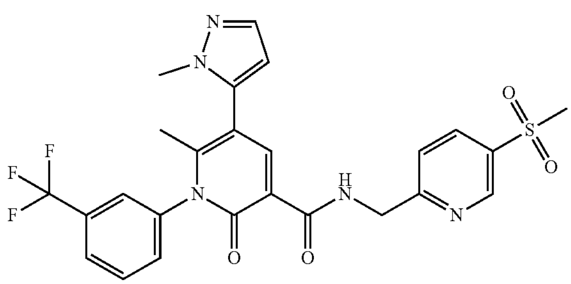 [SMILES: Cc1c(-c2ccnn2C)cc(C(=O)NCc2ccc(S(C)(=O)=O)cn2)c(=O)n1-c1cccc(C(F)(F)F)c1] |
| Alvelestat (36) |
| 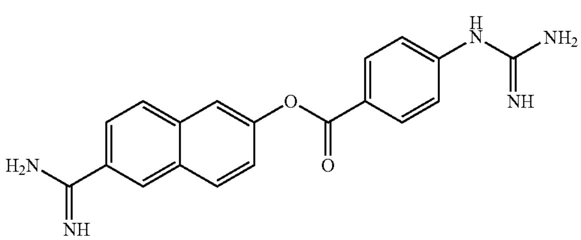 [SMILES: N=C(N)Nc1ccc(C(=O)Oc2ccc3cc(C(=N)N)ccc3c2)cc1] |
| Nafamostat Mesylate (37) |
| 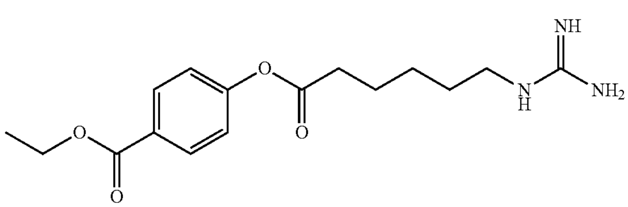 [SMILES: CCOC(=O)c1ccc(OC(=O)CCCCCNC(=N)N)cc1] |
| Gabexate (38) |

TABLE 1-continued
| List of protease inhibitors tested against SARS-CoV-2 Mpro. |
| --- |
| 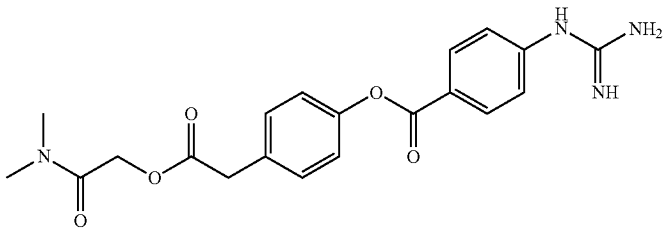 [SMILES: CN(C)C(=O)COC(=O)Cc1ccc(OC(=O)c2ccc(NC(=N)N)cc2)cc1] |
| Camostat Mesilate (39) |
| Cathepsin and calpain protease (cysteine protease) inhibitors |
| 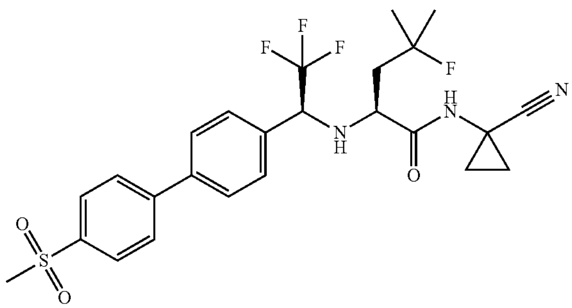 [SMILES: CC(C)(F)C[C@H](N[C@@H](c1ccc(-c2ccc(S(C)(=O)=O)cc2)cc1)C(F)(F)F)C(=O)NC1(C#N)CC1] |
| Odanacatib (MK-0822) (40) |
| 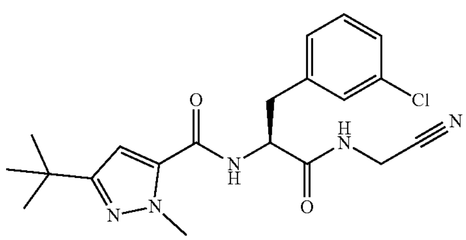 [SMILES: Cn1nc(C(C)(C)C)cc1C(=O)N[C@@H](Cc1cccc(Cl)c1)C(=O)NCC#N] |
| Cathepsin Inhibitor 1 (41) |
| 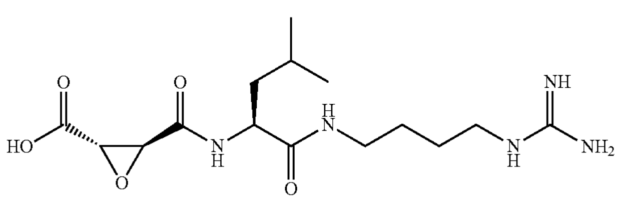 [SMILES: CC(C)C[C@H](NC(=O)[C@H]1O[C@@H]1C(=O)O)C(=O)NCCCCNC(=N)N] |
| E-64 (42) |
| 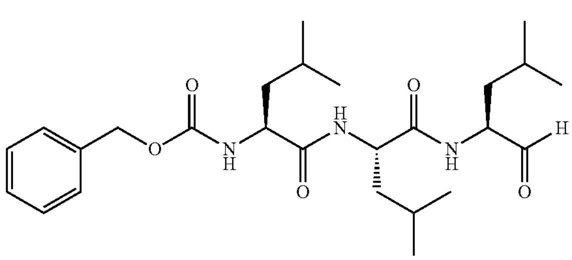 [SMILES: CC(C)C[C@@H](C=O)NC(=O)[C@H](CC(C)C)NC(=O)[C@H](CC(C)C)NC(=O)OCc1ccccc1] |
| MG-132 (43) |

TABLE 1-continued
| List of protease inhibitors tested against SARS-CoV-2 Mpro. |
| --- |
| Miscellaneous cysteine protease inhibitors |
| 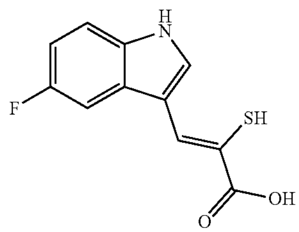 [SMILES: O=C(O)/C(S)=C/c1c[nH]c2ccc(F)cc12] |
| PD151746 (44) |
| 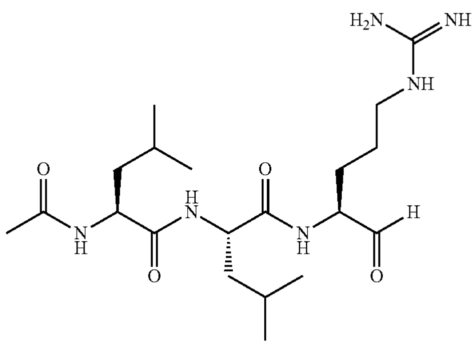 [SMILES: CC(=O)N[C@@H](CC(C)C)C(=O)N[C@@H](CC(C)C)C(=O)N[C@H](C=O)CCCNC(=N)N] |
| Leupeptin (45) |
| 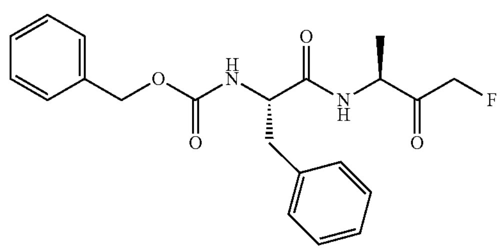 [SMILES: C[C@H](NC(=O)[C@H](Cc1ccccc1)NC(=O)OCc1ccccc1)C(=O)CF] |
| Z-FA-FMK (46) |
| 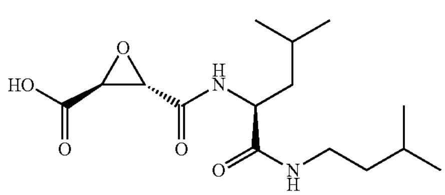 [SMILES: CC(C)CCNC(=O)[C@H](CC(C)C)NC(=O)[C@H]1O[C@@H]1C(=O)O] |
| Loxistatin Acid (47) |
| 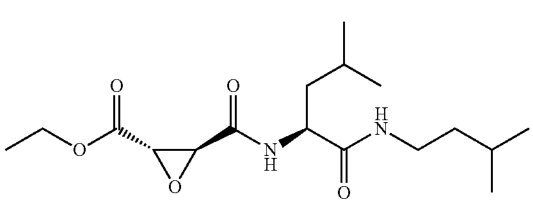 [SMILES: CCOC(=O)[C@H]1O[C@@H]1C(=O)N[C@@H](CC(C)C)C(=O)NCCC(C)C] |
| Aloxistatin (48) |

TABLE 1-continued
| List of protease inhibitors tested against SARS-CoV-2 Mpro. |
| --- |
| Matrix metallprotease inhibitors |
| 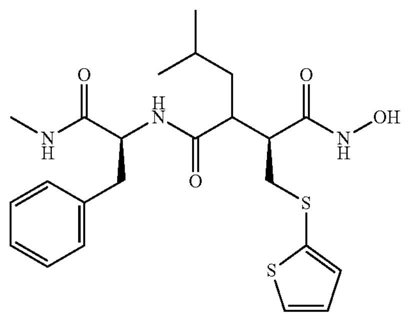 [SMILES: CNC(=O)[C@H](Cc1ccccc1)NC(=O)C(CC(C)C)[C@H](CSc1cccs1)C(=O)NO] |
| Batimastat (BB-94) (49) |
| 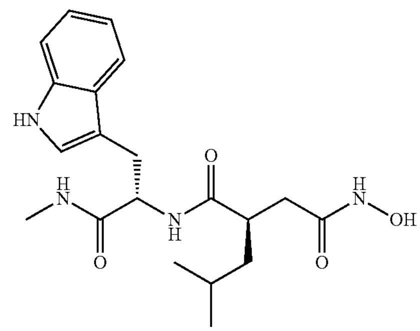 [SMILES: CNC(=O)[C@H](Cc1c[nH]c2ccccc12)NC(=O)[C@@H](CC(=O)NO)CC(C)C] |
| Ilomastat (50) |
| 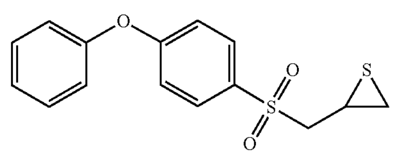 [SMILES: O=S(=O)(CC1CS1)c1ccc(Oc2ccccc2)cc1] |
| SB-3CT (51) |
| Miscellaneous protease inhibitors |
| 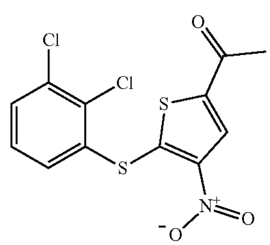 [SMILES: CC(=O)c1cc([N+](=O)[O-])c(Sc2cccc(Cl)c2Cl)s1] |
| P5091 (P005091) (52) |
| 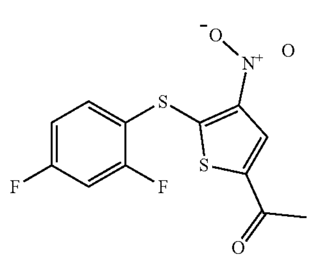 |
| P22077 (53) |

TABLE 1-continued

List of protease inhibitors tested against SARS-CoV-2 Mpro.

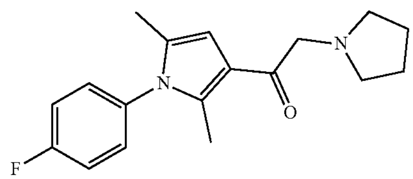 [SMILES: Cc1cc(C(=O)CN2CCCC2)c(C)n1-c1ccc(F)cc1]

IU1 S7134 (54)

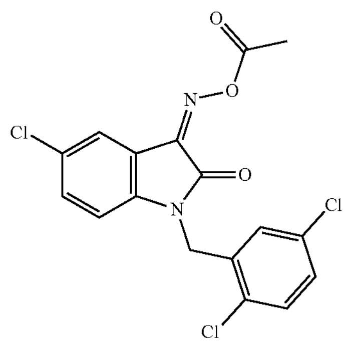 [SMILES: CC(=O)O/N=C1\C(=O)N(Cc2cc(Cl)ccc2Cl)c2ccc(Cl)cc21]

LDN-57444 (55)

Secondary Screening of a Focused Library of Calpain/Cathepsin Inhibitors and Known Viral $3CL^{pro}$ Inhibitors Given the encouraging results from the primary screening, we then further characterized the four hits (24, 28, 29, and 43) in a consortium of assays including dose-response titration, thermal shift binding assay (TSA), and counter screening assays with two other viral cysteine proteases, the enterovirus A71 (EV-A71) 2A and 3C proteases, both of which are cysteine proteases. The HCV NS3-4A protease inhibitors boceprevir (28) and narlaprevir (29) inhibited $M^{pro}$ with $IC_{50}$ values of 4.13 and 4.73 μM, respectively (Table 2), more potent than simeprevir (24) ($IC_{50}$=13.74 μM). Both compounds 28 and 29 also showed strong binding towards $M^{pro}$ and shifted the melting temperature of the protein ($\Delta T_m$) by 6.67 and 5.18° C., respectively, at 30 μM. Despite their potent inhibition against the HCV NS3-4A serine protease and the SARS-CoV-2 cysteine $M^{pro}$, boceprevir (28) and narlaprevir (29) did not inhibit the EV-A71 2A and 3C proteases ($IC_{50}$>20 μM), suggesting they are not non-specific cysteine protease inhibitors. The calpain inhibitor MG-132 (43) had an $IC_{50}$ value of 3.90 μM against the $M^{pro}$, and was not active against the EV-A71 2A and 3C proteases ($IC_{50}$>20 μM). The binding of MG-132 (43) to $M^{pro}$ was also confirmed in the TSA assay with a $\Delta T_m$ of 4.02° C.

In light of the promising results of the calpain inhibitor MG-132 (43), we then pursued to testing other calpain and cathepsin inhibitors that are commercially available (56-63) (Table 2). Among this series of analogs, calpain inhibitor II (61) and XII (62) are the most potent $M^{pro}$ inhibitors with $IC_{50}$ values of 0.97 and 0.45 μM, respectively. Binding of compounds 61 and 62 to $M^{pro}$ shifted the melting curve of the protein by 6.65 and 7.86° C., respectively. Encouragingly, both compounds 61 and 62 did not inhibit the EV-A71 2A and 3C proteases ($IC_{50}$>20 μM). Calpain inhibitor I (59) and MG-115 (60) also showed potent inhibition against $M^{pro}$ with $IC_{50}$ values of 8.60 and 3.14 μM, respectively. Calpeptin (56) and PSI (63) had moderate activity against $M^{pro}$ with $IC_{50}$ values of 10.69 and 10.38 μM, respectively. In contrast, calpain inhibitors III (57) and VI (58) were not active ($IC_{50}$>20 μM).

We also included two well-known viral 3CL protease inhibitors GC-376 (64) and rupintrivir (65) in the secondary screening. GC-376 (64) is an investigational veterinary drug that is being developed for feline infectious peritonitis (FIP). GC-376 (64) was designed to target the viral 3CL protease and had potent antiviral activity against multiple viruses including MERS, FIPV, and norovirus (see, Pedersen, N. C.; et al., J Feline Med Surg 2018, 20 (4), 378-392; Kim, Y.; et al., Journal of virology 2012, 86 (21), 11754-62). Rupintrivir (65) was developed as a rhinovirus antiviral by targeting the viral 3CL protease, but it was discontinued in clinical trials due to side effects. In our study, we found that GC-376 (64) was the most potent $M^{pro}$ inhibitor with an $IC_{50}$ value of 0.03 μM. It shifted the melting curve of $M^{pro}$ by 18.30° C. upon binding. In contrast, rupintrivir (65) was not active against $M^{pro}$ ($IC_{50}$>20 μM). Both compounds 64 and 65 were not active against the EV-A71 2A protease, but showed potent inhibition against the EV-A71 3C protease, which is consistent with previously reported results (see, Kim, Y.; et al., Journal of virology 2012, 86 (21), 11754-62; Musharrafieh, R.; et al., Journal of virology 2019, 93 (7); Kuo, C.-J.; et al., Bioorganic & Medicinal Chemistry 2008, 16 (15), 7388-7398).

Rupintrivir was reported to be not active against the SARS-CoV $3CL^{pro}$ ($IC_{50}$>100 μM) (see, Shie, J. J., et al., Bioorganic & Medicinal Chemistry 2005, 13 (17), 5240-5252).

TABLE 2

| Inhibition by focused library of HCV and calpain proteases inhibitors[a] | | | | | |
|---|---|---|---|---|---|
| ID/Results | SARS-CoV-2 $M^{pro}$ $IC_{50}$ (μM) | 2019-nCoV 3CL TSA Tm/ΔTm (° C) | EVA71 2A $IC_{50}$ (μM) | EV-A71 3C $IC_{50}$ (μM) | Development stage |
| DMSO | — | 55.74 ± 0.00 | — | — | |
| 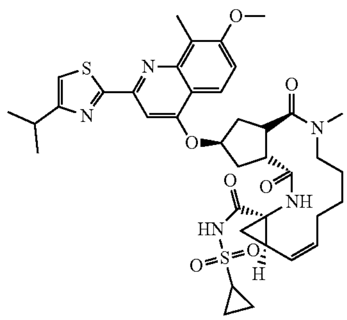 Simeprevir (24) | 13.74± | N.T. | N.T. | N.T. | FDA-approved HCV drug |
| 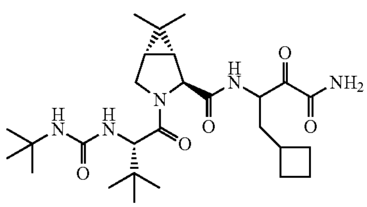 [SMILES: CC(C)(C)NC(=O)N[C@H](C(=O)N1C[C@H]2[C@@H]([C@H]1C(=O)NC(CC1CCC1)C(=O)C(N)=O)C2(C)C)C(C)(C)C] Boceprevir (28) | 4.13 ± 0.61 | 62.41 ± 0.21/6.67 | >20 | >20 | FDA-approved HCV drug |
| 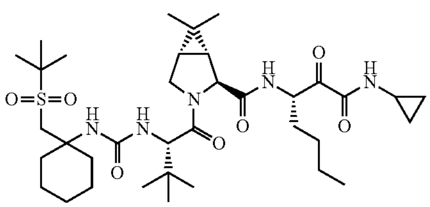 [SMILES: CCCC[C@H](NC(=O)[C@@H]1[C@@H]2[C@H](CN1C(=O)[C@@H](NC(=O)NC1(CS(=O)(=O)C(C)(C)C)CCCCC1)C(C)(C)C)C2(C)C)C(=O)C(=O)NC1CC1] Narlaprevir (29) | 5.73 ± 0.67 | 60.92 ± 0.14/5.18 | >20 | >20 | FDA-approved HCV drug |
| 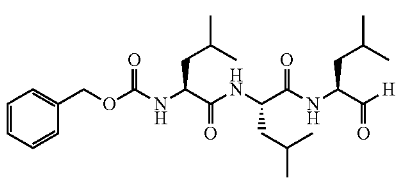 [SMILES: CC(C)C[C@@H](C=O)NC(=O)[C@H](CC(C)C)NC(=O)[C@H](CC(C)C)NC(=O)OCc1ccccc1] MG-132 (ApexBio) (43) | 3.90 ± 1.01 | 59.76 ± 0.45/4.02 | >20 | >20 | Preclinical; tested in mice[13] |
| 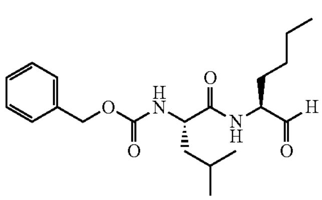 [SMILES: CCCC[C@@H](C=O)NC(=O)[C@H](CC(C)C)NC(=O)OCc1ccccc1] Calpeptin (56) | 10.69 ± 2.77 | 56.84 ± 0.00/1.1 | >20 | >20 | Preclinical; tested in mice and feline[14-15] |

TABLE 2-continued

Inhibition by focused library of HCV and calpain proteases inhibitors[a]

| ID/Results | SARS-CoV-2 $M^{pro}$ $IC_{50}$ (μM) | 2019-nCoV 3CL TSA Tm/ΔTm (° C) | EVA71 2A $IC_{50}$ (μM) | EV-A71 3C $IC_{50}$ (μM) | Development stage |
|---|---|---|---|---|---|
| 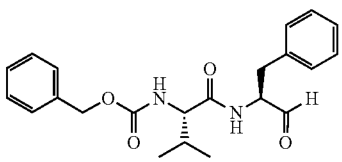 [SMILES: CC(C)[C@H](NC(=O)OCc1ccccc1)C(=O)N[C@H](C=O)Cc1ccccc1] calpain inhibitor III (MDL28170) (57) | >20 | 55.36 ± 0.14/−0.38 | N.T.[b] | N.T. | Preclinical; not tested in animal model |
| 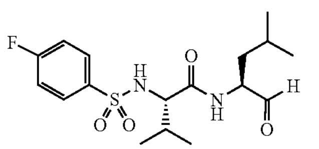 [SMILES: CC(C)C[C@@H](C=O)NC(=O)[C@@H](NS(=O)(=O)c1ccc(F)cc1)C(C)C] Calpain inhibitor VI (58) | >20 | 55.46 ± 0.14/−0.28 | N.T. | >20 | Preclinical; tested in rats[16] |
| 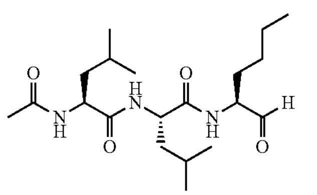 [SMILES: CCCC[C@@H](C=O)NC(=O)[C@H](CC(C)C)NC(=O)[C@H](CC(C)C)NC(C)=O] Calpain inhibitor 1 (ALLN) (59) | 8.60 ± 1.46 | N.T. | >20 | >20 | Preclinical; tested in mice[17] |
| 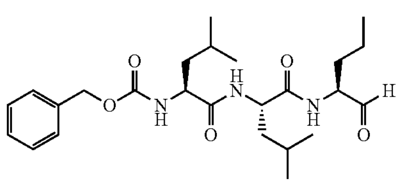 [SMILES: CCC[C@@H](C=O)NC(=O)[C@H](CC(C)C)NC(=O)[C@H](CC(C)C)NC(=O)OCc1ccccc1] MG-115 (60) | 3.14 ± 0.97 | 60.51 ± 0.28/4.77 | >20 | >20 | Preclinical; not tested in animal model |
| 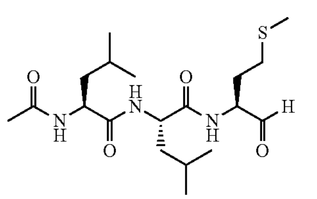 [SMILES: CSCC[C@@H](C=O)NC(=O)[C@H](CC(C)C)NC(=O)[C@H](CC(C)C)NC(C)=O] Calpain inhibitor II (ALLM) (61) | 0.97 ± 0.27 | 62.93 ± 0.14/6.65 | >20 | >20 | Preclinical; not tested in animal model |
| 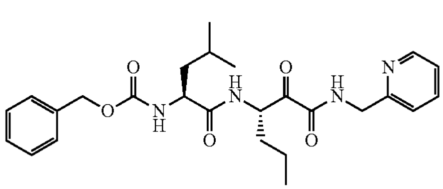 [SMILES: CCC[C@H](NC(=O)[C@H](CC(C)C)NC(=O)OCc1ccccc1)C(=O)C(=O)NCc1ccccn1] Calpain inhibitor XII (62) | 0.45 ± 0.06 | 63.60 ± 0.01/7.86 | >20 | >20 | Preclinical; not tested in animal model |

TABLE 2-continued

Inhibition by focused library of HCV and calpain proteases inhibitors[a]

| ID/Results | SARS-CoV-2 $M^{pro}$ $IC_{50}$ (μM) | 2019-nCoV 3CL TSA Tm/ΔTm (° C) | EVA71 2A $IC_{50}$ (μM) | EV-A71 3C $IC_{50}$ (μM) | Development stage |
|---|---|---|---|---|---|
| 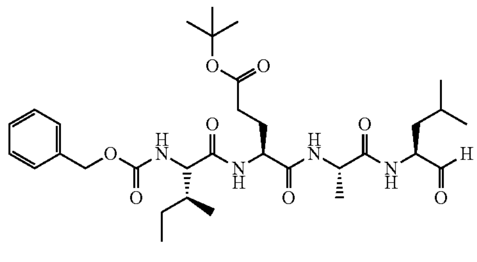 PSI (63) | 10.38 ± 2.90[c] | N.T. | 1.22 | 13.74 ± 3.86 | Preclinical; tested in rats[18] |
| 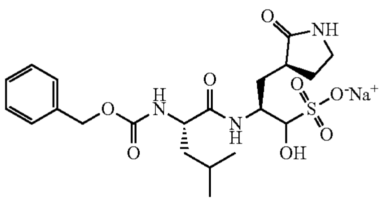 GC376 (more reliable) (64) | 0.030 ± 0.008 | 74.04 ± 0.07/18.30 | >20 | 0.136 ± 0.025 | Preclinical; tested in feline[8,19] |
| 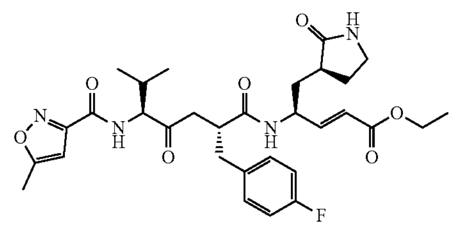 [SMILES: CCOC(=O)/C=C/[C@H](C[C@@H]1CCNC1=O)NC(=O)[C@@H](CC(=O)[C@@H](NC(=O)c1cc(C)on1)C(C)C)Cc1ccc(F)cc1] Rupintrivir (65) | >20 | N.T. | >20 | 0.042 ± 0.014 | Dropped out of clinical trial |

[a]Value = mean ± S.E. from 2 to 3 independent experiments;

[b]N.T. means not tested;

[c]The $IC_{50}$ of PSI (64) on SARS CoV-2 $M^{pro}$ was calculated by end point reading of 1 hour digestion, instead of the initial velocity.

Figure 3:
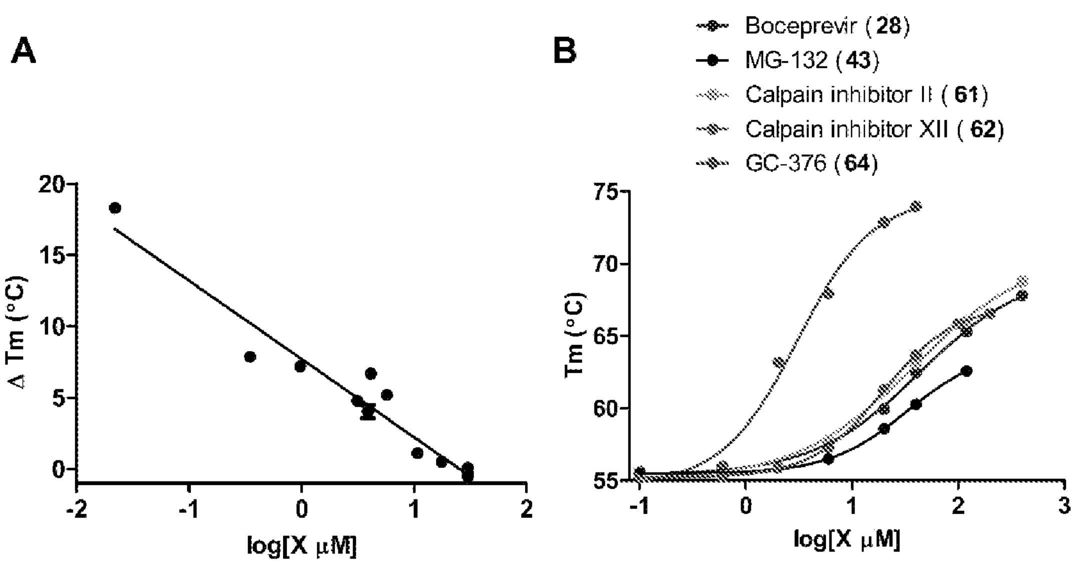
FIG. 3: Binding of inhibitors to SARS-CoV-2 $M^{pro}$ using thermal shift binding assay. (A) Correlation of inhibition efficacy ($IC_{50}$) with $\Delta T_m$ from thermal shift binding assay. Data in Table 2 were used for the plot. The $r^2$ of fitting is 0.94. (B) Dose-dependent melting temperature ($T_m$) shift.

When plotting the $IC_{50}$ values (log scale) of the inhibitors against $M^{pro}$ from the FRET enzymatic assay with the melting temperature shifts ($\Delta T_m$) from thermal shift binding assay (FIG. 3A), a linear correlation was observed, and the $r^2$ of the linear regression fitting is 0.94. This suggests that there is a direct correlation between the enzymatic inhibition and protein binding: a more potent enzyme inhibitor also binds to the protein with higher affinity. The stabilization of the $M^{pro}$ against thermal denaturation was also compound concentration dependent (FIG. 3B).

Mechanism of Action of Hits

Figure 4:
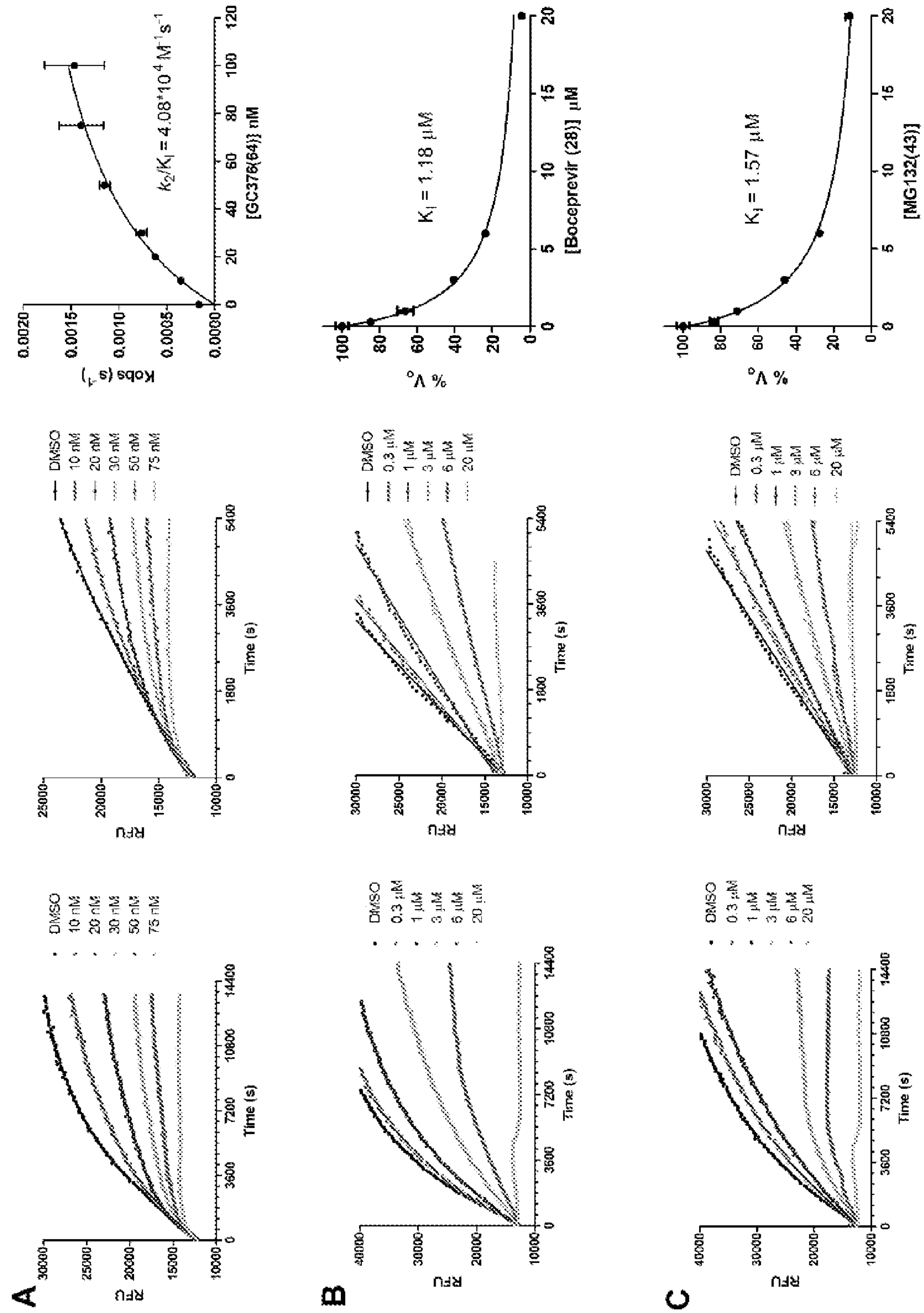
FIG. 4: Proteolytic reaction progression curves of $M^{pro}$ in the presence or the absence of compounds. In the kinetic studies, 5 nM $M^{pro}$ was added to a solution containing various concentrations of protease inhibitors and 20 μM FRET substrate to initiate the reaction, the reaction was then monitored for 4 hrs. Left column shows the reaction progression up to 4 hrs; middle column shows the progression curves for the first 90 min, which were used for curve fitting to generate the plot shown in the right column. Detailed methods were described in the Method section. (A) GC-376 (64); (B) Boceprevir (28); (C) MG-132 (43); (D) Calpian inhibitor II (61); (E) Calpain inhibitor XII (62).
Figure 4:
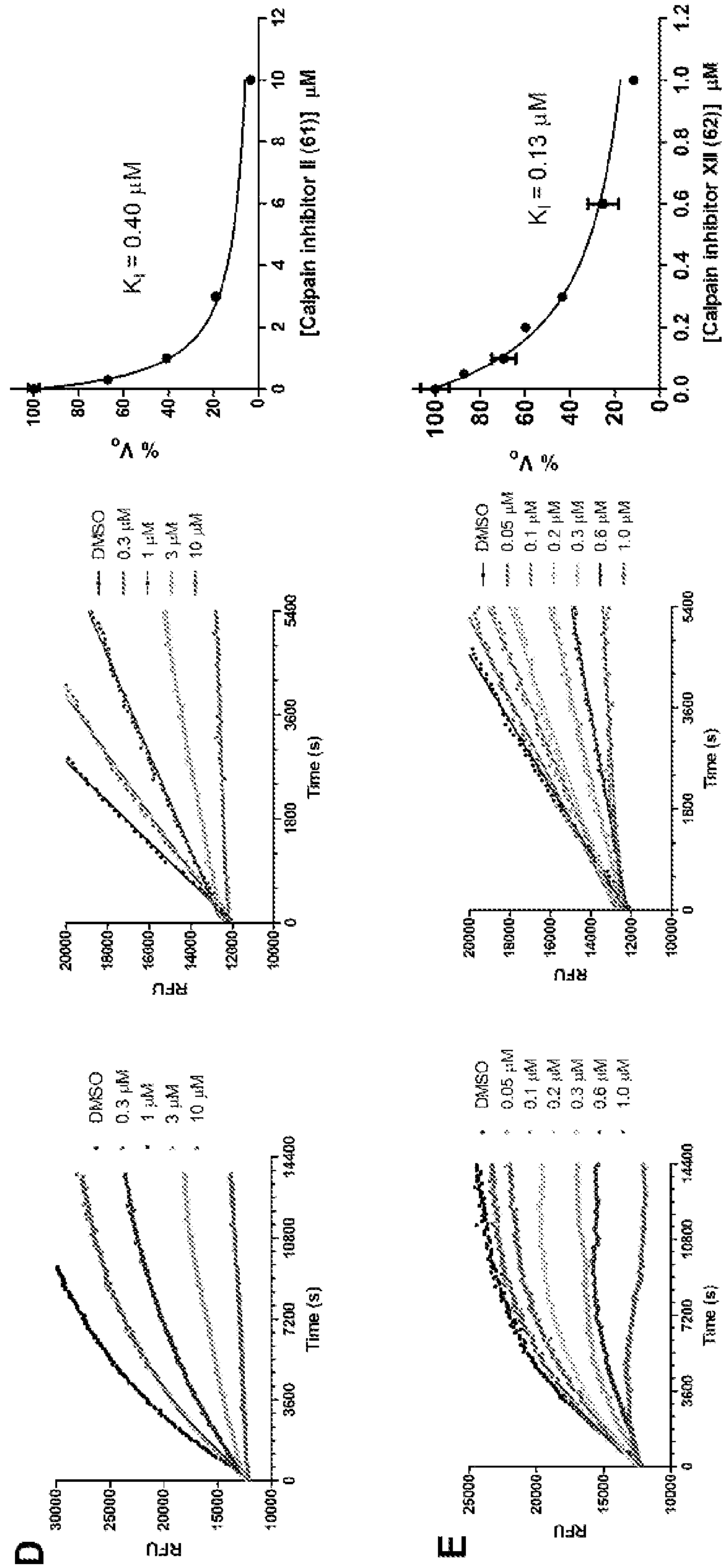

To elucidate the mechanism of action of hits against $M^{pro}$, we focus on five most potent compounds prioritized from the primary and secondary screenings including boceprevir (28), MG-132 (43), calpain inhibitor II (61), calpain inhibitor XII (62), and GC-376 (64). For this, we performed enzyme kinetic studies with different concentrations of inhibitors (FIG. 4). A biphasic character in the presence but not in the absence of inhibitor in the kinetic curve (RFU vs time) is typically a hallmark for a slow covalent binding inhibitor. In the FIG. 4, left column shows the progression curves up to 4 hours. Biphasic progression curves were observed for all 5 inhibitors at high drug concentrations. Significant substrate depletion was observed when the proteolytic reaction proceeded beyond 90 minutes, we therefore chose the first 90 minutes of the progression curves for curve fitting (FIG. 4 middle column). We fit the progression curves in the presence different concentrations of GC-376 (64) with the two-step Morrison equation (equation 3 in methods section). GC-376 (64) binds to SARS-CoV-2 $M^{pro}$ with an equilibrium dissociation constant for the inhibitor (KO of 59.9±21.7 nM in the first step. After initial binding, a slower covalent bond is formed between GC-376 (64) and $M^{pro}$ with the second reaction rate constant ($k_2$) being 0.00245±0.00047 $s^{-1}$, resulting an overall $k_2/K_I$ value of $4.08\times10^4$ $M^{-1}$ $s^{-1}$ (FIG. 4A). However, when we tried to fit the proteolytic progression curves for boceprevir (28), MG-132 (43), calpain inhibitors II (61) and XII (62) using the same two-step reaction mechanism, we could not obtain accurate values for the second rate constant ($k_2$). This is presumably due to significant substrate depletion before the equilibrium between EI and EI*, leading to very small values of $k_2$. Accordingly, for these four inhibitors 28, 43, 61, and 62, only the dissociation constant $K_I$ values from the first step were determined (FIGS. 6B-6E). The inhibition constants ($K_I$) for boceprevir (28), MG-132 (43), calpain inhibitors II (61) and XII (62) are 1.18±0.10 μM, 1.57±0.13 μM, 0.40±0.02 μM, and 0.13±0.02 μM, respectively.

Cellular Antiviral Activity and Cytotoxicity of Hits

To test the hypothesis that inhibiting the enzymatic activity of $M^{pro}$ will lead to the inhibition of SARS-CoV-2 viral replication, we performed cellular antiviral assays for the five promising hits 64, 28, 43, 61, and 62 against SARS-CoV-2. For this, we first tested the cellular cytotoxicity of these compounds in multiple cell lines (Table 3). GC-376 (64), boceprevir (28), and calpain inhibitor II (61) were well tolerated and had $CC_{50}$ values of over 100 μM for all the cell lines tested. MG-132 (43) was cytotoxic to all the cells with $CC_{50}$ values less than 1 μM except A549 cells. Calpain inhibitor XII (62) had acceptable cellular cytotoxicity with $CC_{50}$ values above 50 μM for all the cell lines tested.

TABLE 3

Selected protease inhibitors cytotoxicity on various cell lines[a]

| | GC-376 (64) | Boceprevir (28) | MG-132 (43) | Calpain inhibitor II (61) | Calpain inhibitor XII (62) |
|---|---|---|---|---|---|
| MDCK | >100 | >100 | 0.34 ± 0.02 | >100 | 60.36 ± 2.28 |
| Vero | >100 | >100 | 0.45 ± 0.02 | >100 | >100 |
| HCT-8 | >100 | >100 | 0.47 ± 0.02 | >100 | 73.29 ± 11.80 |
| A549 | >100 | >100 | 10.71 ± 3.50 | >100 | >100 |
| Caco-2 | >100 | >100 | <0.15 | >100 | 82.02 ± 0.37 |
| BEAS2B | >100 | >100 | 0.14 ± 0.03 | >100 | 78.91 ± 13.70 |

[a]Cytotoxicity was evaluated by measuring $CC_{50}$ values (50% cytotoxic concentration) with CPE assay described in the method section. $CC_{50}$ = mean ± S.E. of 2 or 3 independent experiments.

TABLE 4

Antiviral activity of hits against SARS-CoV-2, SARS-CoV, MERS-CoV in CPE assays and counter screening against influenza virus in plaque assay.

| | GC-376 (64) (μM) | Boceprevir (28) (μM) | MG-132 (43) (μM) | Calpain inhibitor II (61) (μM) | Calpain inhibitor XII (62) (μM) |
|---|---|---|---|---|---|
| SARS-CoV-2 | $EC_{50}$ = 1.9<br>$CC_{50}$ > 100<br>SI > 53 | $EC_{50}$ = 1.9<br>$CC_{50}$ > 100<br>SI > 53 | $EC_{50}$ = 0.87<br>$CC_{50}$ > 10<br>SI > 110 | $EC_{50}$ = 1.2<br>$CC_{50}$ > 100<br>SI > 83 | $EC_{50}$ = 0.3<br>$CC_{50}$ > 50<br>SI > 170 |
| SARS-CoV | $EC_{50}$ = 9.6<br>$CC_{50}$ > 100<br>SI > 10 | $EC_{50}$ > 47<br>$CC_{50}$ > 47 | $EC_{50}$ > 0.7<br>$CC_{50}$ > 0.7 | $EC_{50}$ = 3.6<br>$CC_{50}$ > 100<br>SI > 28 | $EC_{50}$ = 7.4<br>$CC_{50}$ = 23<br>SI = 3.1 |
| MERS-CoV | $EC_{50}$ = 5.6<br>$CC_{50}$ > 100<br>SI > 18 | $EC_{50}$ > 100<br>$CC_{50}$ > 100 | $EC_{50}$ > 10<br>$CC_{50}$ > 10 | $EC_{50}$ = 14<br>$CC_{50}$ > 100<br>SI > 7.1 | $EC_{50}$ = 7.9<br>$CC_{50}$ > 50<br>SI > 6.3 |
| A/California/07/2009 (H1N1) | >20 | >20 | N.T. | >20 | >20 |

Discussion

Coronaviruses have caused three epidemics/pandemics in the past twenty years including SARS, MERS, and COVID-19. With the ongoing pandemic of COVID-19, scientists and researchers around the globe are racing to find effective vaccines and antiviral drugs. The viral polymerase inhibitor remdesivir holds the greatest promise and it is currently being evaluated in several clinical trials. The HIV drug combination lopinavir and ritonavir recently failed in a clinical trial for COVID-19 with no significant therapeutic efficacy was observed. To address this unmet medical need, we initiated a drug repurposing screening to identify potent inhibitors against the viral $M^{pro}$ from a collection of bioactive compounds. The $M^{pro}$ has been shown to be a validated antiviral drug target for SARS and MERS. As the SARS-CoV-2 $M^{pro}$ shares a high sequence similarity with SARS and to a less extent with MERS, we reasoned that inhibiting the enzymatic activity of SARS-CoV-2 $M^{pro}$ will similarly prevent viral replication. Noticeable findings from our study include: 1) Boceprevir (28), an FDA-approved HCV drug, inhibits the enzymatic activity of $M^{pro}$ with $IC_{50}$ of 4.13 μM, and has an $EC_{50}$ of X μM against the SARS-CoV-2 virus in the cellular viral cytopathic effect assay. For comparison, the $IC_{50}$ of remdesivir against SARS-CoV-2 in cell culture is 0.77 μM (see, Wang, M.; et al., Cell Res 2020, 30 (3), 269-271). The therapeutic potential of boceprevir (28) should be further evaluated in relevant animal models and human clinic trials. Since this is a FDA-approved drug, the dose, toxicity, formulation, and pharmacokinetic properties are already known, which will greatly speed up the design of follow up studies; 2) GC-376 (64), an investigational veterinary drug, showed promising antiviral activity against the SARS-CoV-2 virus. It has the highest enzymatic inhibition against the $M^{pro}$ with an $IC_{50}$ value of 0.03 μM. This compound has promising in vivo efficacy in treating cats infected with FIP, and has favorable in vivo pharmacokinetic properties. Therefore, GC-376 (64) is ready to be tested in relevant animal models of SARS-CoV-2 when available; 3) Three calpain/cathepsin inhibitors, GC-376 (64), calpain inhibitors II (61) and XII (62), are potent inhibitors of $M^{pro}$ and inhibit SARS-CoV-2 with single-digit to submicromolar efficacy. This result suggests that calpain/cathepsin inhibitors are rich sources of drug candidates for SARS-CoV-2. A significant number of calpain/cathepsin inhibitors have been developed over the years for various diseases including cancer, neurodegeneration disease, kidney diseases, and ischemia/reperfusion injury (see, Ono, Y.; et al., Nature reviews. Drug discovery 2016, 15 (12), 854-876). It might be worthwhile to repurposing them as antivirals for SARS-CoV-2.

Methods

Cell lines and viruses. Human rhabdomyosarcoma (RD); A549, MDCK, Caco-2, and Vero cells were maintained in Dulbecco's modified Eagle's medium (DMEM), BEAS2B and HCT-8 cells were maintained in RPMI 1640 medium. Both medium was supplemented with 10% fetal bovine serum (FBS) and 1% penicillin-streptomycin antibiotics. Cells were kept at 37° C. in a 5% CO2 atmosphere.

Protein expression and purification. SARS CoV-2 Main protease (3CL) gene from strain BetaCoV/Wuhan/WIV04/2019 was ordered from GenScript (Piscataway, NJ) in the pET29a(+) vector with *E. coli* codon optimization. pET29a (+) plasmids with SARS CoV-2 Main protease was transformed into competent *E. coli* BL21(DE3) cells, and a single colony was picked and used to inoculate 10 ml of LB supplemented with 50 g/ml kanamycin at 37° C. and 250 rpm. The 10-ml inoculum was added to 1 liter of LB with 50 g/ml kanamycin and grown to an optical density at 600 nm of 0.8, then induced using 1.0 mM IPTG. Induced cultures were incubated at 37° C. for an additional 3 h and then harvested, resuspended in lysis buffer (25 mM Tris [pH 7.5], 750 mM NaCl, 2 mM dithiothreitol [DTT] with 0.5 mg/ml lysozyme, 0.5 mM phenylmethylsulfonyl fluoride [PMSF], 0.02 mg/ml DNase I), and lysed with alternating sonication and French press cycles. The cell debris were removed by centrifugation at 12,000 g for 45 min (20% amplitude, 1 s on/1 s off). The supernatant was incubated with Ni-NTA resin for over 2 h at 4° C. on a rotator. The Ni-NTA resin was thoroughly washed with 30 mM imidazole in wash buffer (50 mM Tris [pH 7.0], 150 mM NaCl, 2 mM DTT); and eluted with 100 mM imidazole in 50 mM Tris [pH 7.0], 150 mM NaCl, 2 mM DTT. The imidazole was removed via dialysis or on a 10,000-molecular-weight-cutoff centrifugal concentrator spin column. The purity of the protein was confirmed with SDS-PAGE. The protein concentration was determined via 260 nM absorbance with c 32890. EV-A71 2Apro and 3Cpro were expressed in the pET28b(+) vector as previously described (see, Musharrafieh, R.; et al., Journal of virology 2019, 93 (7); Shang, L.; et al., Antimicrob Agents Chemother 2015, 59 (4), 1827-36; Cai, Q.; et al., Journal of virology 2013, 87 (13), 7348-56).

Peptide Synthesis.

Enzymatic assays. For reaction condition optimization, 200 μM SARS CoV-2 Main protease was used. pH6.0 buffer contains 20 mM MES pH6.0, 120 mM NaCl, 0.4 mM EDTA, 4 mM DTT and 20% glycerol; pH6.5 buffer contains 20 mM HEPES pH6.5, 120 mM NaCl, 0.4 mM EDTA, 4 mM DTT and 20% glycerol, pH7.0 buffer contains 20 mM HEPES pH7.0, 120 mM NaCl, 0.4 mM EDTA, 4 mM DTT and 20% glycerol. Upon addition of 20 μM FRET substrate, the reaction progress was monitored for 1 hr. The first 15 min of reaction was used to calculate initial velocity ($V_i$) via linear regression in prism 5. Main protease displays highest proteolytic activity in pH6.5 buffer. All the following enzymatic assays were carried in pH6.5 buffer.

For the measurements of $K_m/V_{max}$, screening the protease inhibitor library, as well as $IC_{50}$ measurements, proteolytic reaction with 100 nM Main protease in 100 μl pH6.5 reaction buffer was carried out at 30° C. in a Cytation 5 imaging reader (Thermo Fisher Scientific) with filters for excitation at 360/40 nm and emission at 460/40 nm. Reactions were monitored every 90 s. For $K_m/V_{max}$ measurements, a FRET substrate concentration ranging from 0 to 200 μM was applied. The initial velocity of the proteolytic activity was calculated by linear regression for the first 15 min of the kinetic progress curves. The initial velocity was plotted against the FRET concentration with the classic Michaelis-Menten equation in Prism 5 software. For the screening protease inhibitor library and $IC_{50}$ measurements, 100 nM Main protease was incubated with protease inhibitor at 30° C. for 30 min in reaction buffer, and then the reaction was initiated by adding 10 μM FRET substrate, the reaction was monitored for 1 h, and the initial velocity was calculated for the first 15 min by linear regression. The $IC_{50}$ was calculated by plotting the initial velocity against various concentrations of protease inhibitors by use of a dose-response curve in Prism 5 software. Dialysis assays were performed by using 5 ml 100 nM Main protease in reaction buffer was preincubated with 5 μl DMSO, or 5 μl 300 μM GC376 (final concentration 300 nM), or 5 μl 20 mM Calpain inhibitor II (final concentration 20 μM), or 5 μl 20 mM Calpain inhibitor XII (final concentration 20 μM) at 30° C. for 30 min, then 100 μl was taken from the mixture and proteolytic activity was measured (Day 0). The remaining mix was loaded into a 10,000-molecular-weight-cutoff dialysis tubing and dialyzed in 2 liters of reaction buffer separately at 4° C. Every 24 h, 100 μl mix were taken to measure the enzymatic activity with 10 μM FRET substrate.

Proteolytic reaction progress curve kinetics measurements with GC376, MG132, Boceprevir, Calpain inhibitor II, and Calpain inhibitor XII used for curve fitting, were carried out as follows: 5 nM Main protease protein was added to 20 μM FRET substrate with various concentrations of testing inhibitor in 200 μl of reaction buffer at 30° C. to initiate the proteolytic reaction. The reaction was monitored for 4 hrs. The progress curves were fit to a slow binding Morrison equation (equation 3) as described previously (see, Musharrafieh, R.; et al., Journal of virology 2019, 93 (7); Morrison, J. F.; Walsh, C. T., Adv Enzymol Relat Areas Mol Biol 1988, 61, 201-301):

$$E + I \underset{k_{-1}}{\overset{k_1}{\leftrightarrow}} EI \underset{k_{-2}}{\overset{k_2}{\leftrightarrow}} EI* \tag{1}$$

$$K_I = k_{-1}/k_1 \tag{2}$$

$$P(t) = P_0 + V_s t - (Vs - V_0)(1 - e^{-kt})/k \tag{3}$$

$$k = k_2[I]/(K_I + [I]) \tag{4}$$

where P(t) is the fluorescence signal at time t, $P_0$ is the background signal at time zero, $V_0$, $V_s$, and and k represent, respectively, the initial velocity, the final steady-state velocity and the apparent first-order rate constant for the establishment of the equilibrium between EI and EI* (see, Morrison, J. F.; et al., Adv Enzymol Relat Areas Mol Biol 1988, 61, 201-301). $k_2/K_I$ is commonly used to evaluate the efficacy for covalent inhibitor. We observed substrate depletion when proteolytic reactions progress longer than 90 min, therefore only first 90 min of the progress curves were used in the curve fitting (FIG. 6 middle column). In this study, we could not accurately determine the $k_2$ for the protease inhibitors: Calpain inhibitor II, MG132, Boceprevir, and Calpain inhibitor XII, due to the very slow $k_2$ in these case: significant substrate depletion before the establishment of the equilibrium between EI and EI*. In these cases, $K_I$ was determined with Morrison equation in Prism 5.

Differential scanning fluorimetry (DSF). The binding of protease inhibitors on Main protease protein was monitored by differential scanning fluorimetry (DSF) using a Thermal Fisher QuantStudio™ 5 Real-Time PCR System. TSA plates were prepared by mixing Main protease protein (final concentration of 3 μM) with inhibitors, and incubated at 30° C. for 30 min. lx SYPRO orange (Thermal Fisher) were added and the fluorescence of the plates were taken under a temperature gradient ranging from 20 to 90° C. (incremental steps of 0.05° C./s). The melting temperature ($T_m$) was calculated as the mid-log of the transition phase from the native to the denatured protein using a Boltzmann model (Protein Thermal Shift Software v1.3). Thermal shift which was represented as $\Delta T_m$ was calculated by subtracting reference melting temperature of proteins in DMSO from the $T_m$ in the presence of compound.

Cytotoxicity measurement. RD, A549, MDCK, HCT-8, Caco-2, Vero, and BEAS2B cells for cytotoxicity CPE assays were seeded and grown overnight at 37° C. in a 5% CO2 atmosphere to ~90% confluence on the next day. Cells were washed with PBS buffer and 200 μl A DMEM with 2% FBS and 1% penicillin-streptomycin, and various concentration of protease inhibitors was added to each well. 48 hrs after addition the protease inhibitors, cells were stained with 66 μg/mL neutral red for 2 h, and neutral red uptake was measured at an absorbance at 540 nm using a Multiskan FC microplate photometer (Thermo Fisher Scientific). The $CC_{50}$ values were calculated from best-fit dose-response curves using GraphPad Prism 5 software.

Table 5 shows SARS-CoV-2 Mpro inhibition IC50 values for compounds of the invention encompassed within Formula I.

TABLE 5

| Structure | SARS-CoV-2 Mpro inhibition IC50 (μM) |
|---|---|
| 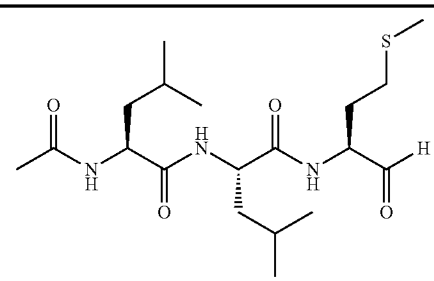 Calpain inhibitor II | 0.97 |
| 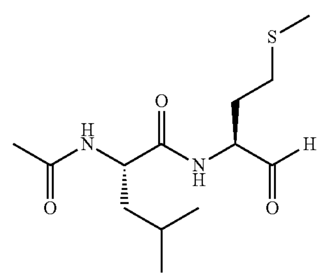 [SMILES: CSCC[C@@H](C=O)NC(=O)[C@H](CC(C)C)NC(C)=O] Jun8-102-1 | 4.77 |
| 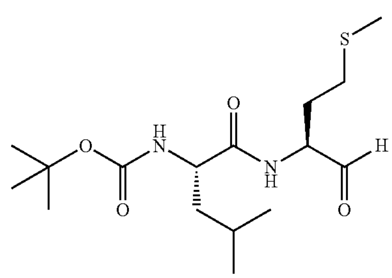 [SMILES: CSCC[C@@H](C=O)NC(=O)[C@H](CC(C)C)NC(=O)OC(C)(C)C] Jun9-2-3 | >20 |
| 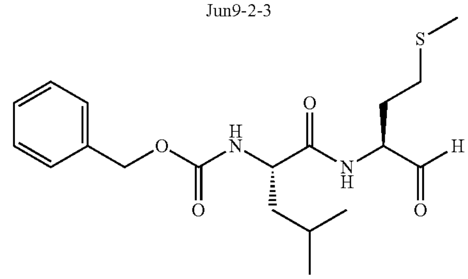 Jun8-102-2 | 0.91 |

TABLE 5-continued
| Structure | SARS-CoV-2 Mpro inhibition IC50 (μM) |
| --- | --- |
| 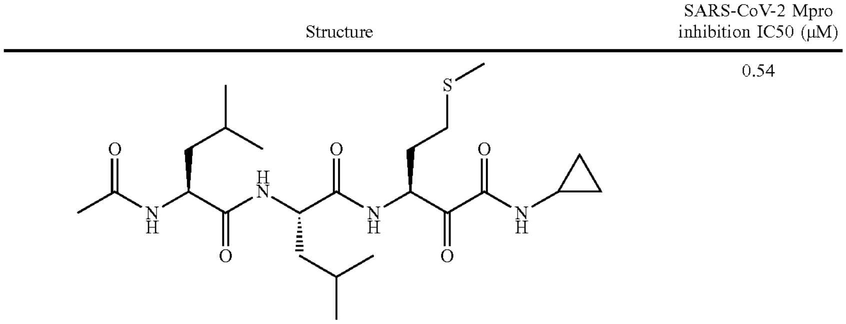 Jun9-11-3 | 0.54 |
| 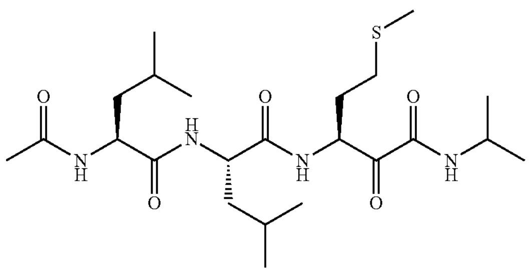 [SMILES: CSCC[C@H](NC(=O)[C@H](CC(C)C)NC(=O)[C@H](CC(C)C)NC(C)=O)C(=O)C(=O)NC(C)C] Jun9-11-4 | 5.99 |
| 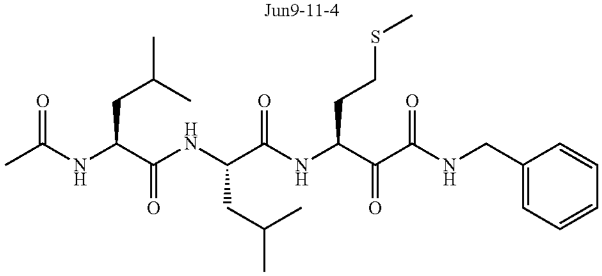 Jun9-11-5 | 1.77 |
| 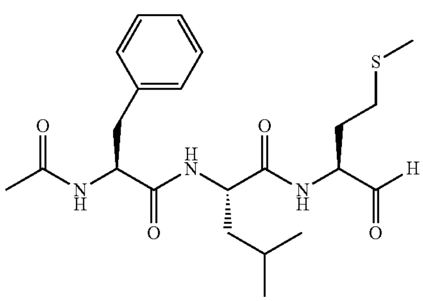 [SMILES: CSCC[C@@H](C=O)NC(=O)[C@H](CC(C)C)NC(=O)[C@H](Cc1ccccc1)NC(C)=O] Jun9-2-5 | 0.27 |
| 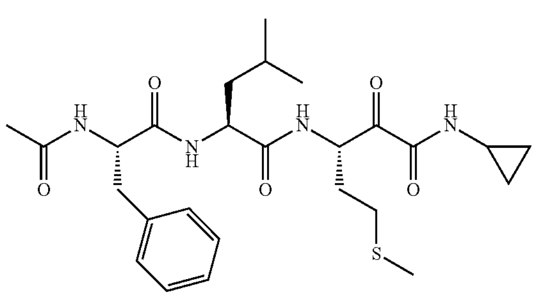 [SMILES: CSCC[C@H](NC(=O)[C@H](CC(C)C)NC(=O)[C@H](Cc1ccccc1)NC(C)=O)C(=O)C(=O)NC1CC1] Jun9-24-3 | 0.46 |

TABLE 5-continued
| Structure | SARS-CoV-2 Mpro inhibition IC50 (μM) |
|---|---|
| 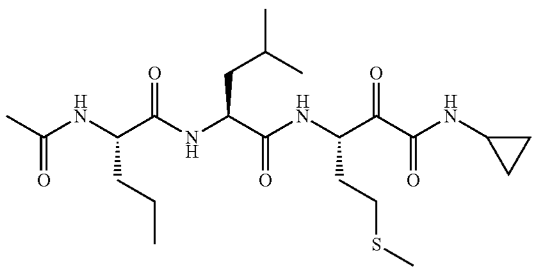 [SMILES: CCC[C@H](NC(C)=O)C(=O)N[C@@H](CC(C)C)C(=O)N[C@@H](CCSC)C(=O)C(=O)NC1CC1] Jun9-24-5 | 0.64 |
| 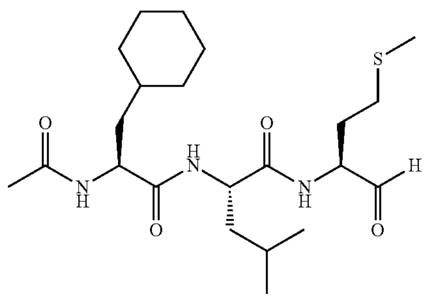 [SMILES: CSCC[C@@H](C=O)NC(=O)[C@H](CC(C)C)NC(=O)[C@H](CC1CCCCC1)NC(C)=O] Jun9-66-2 | 0.29 |
| 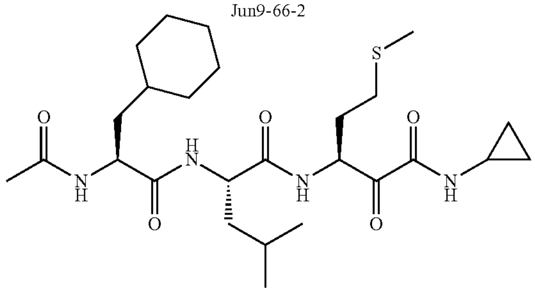 Jun9-66-4 | 0.22 |
| 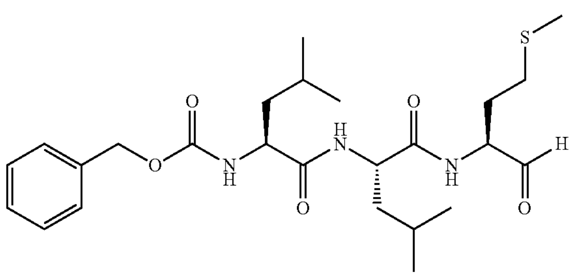 [SMILES: CSCC[C@@H](C=O)NC(=O)[C@H](CC(C)C)NC(=O)[C@H](CC(C)C)NC(=O)OCc1ccccc1] Jun8-61-4 | 0.11 |
| 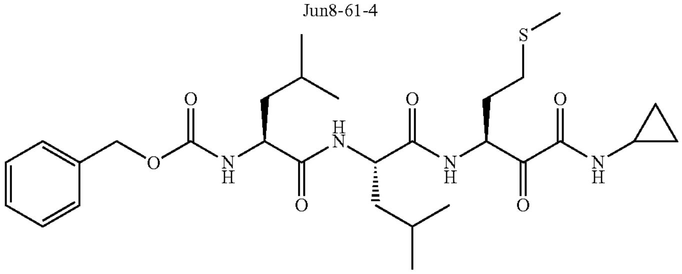 Jun8-43-3 | 2.80 |

TABLE 5-continued
| Structure | SARS-CoV-2 Mpro inhibition IC50 (μM) |
|---|---|
| 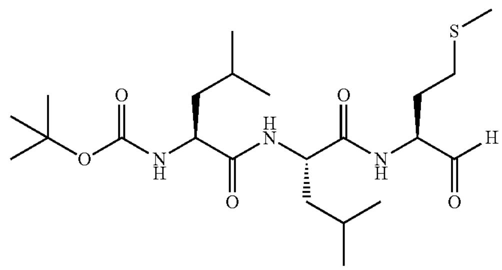 [SMILES: CSCC[C@@H](C=O)NC(=O)[C@H](CC(C)C)NC(=O)[C@H](CC(C)C)NC(=O)OC(C)(C)C] Jun9-2-4 | 0.39 |
| 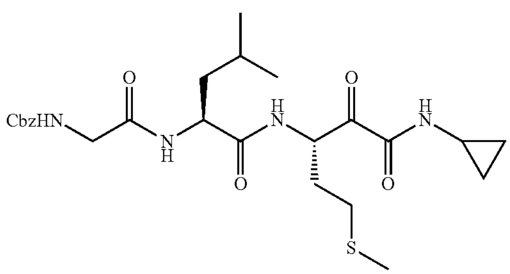 [SMILES: CSCC[C@H](NC(=O)[C@H](CC(C)C)NC(=O)CNC(=O)OCc1ccccc1)C(=O)C(=O)NC1CC1] Jun9-47-4 | 1.20 |
| 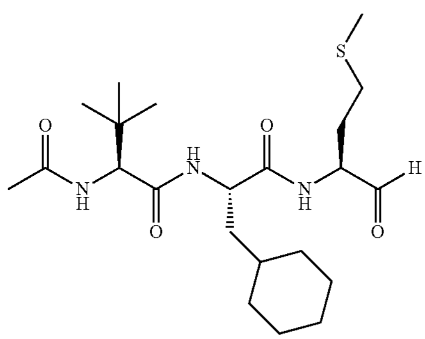 [SMILES: CSCC[C@@H](C=O)NC(=O)[C@H](CC1CCCCC1)NC(=O)[C@@H](NC(C)=O)C(C)(C)C] Jun9-66-1 | 0.32 |
| 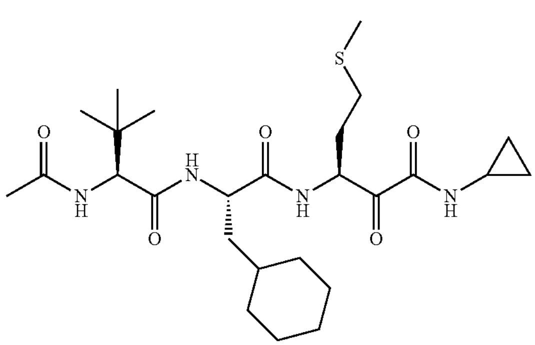 [SMILES: CSCC[C@H](NC(=O)[C@H](CC1CCCCC1)NC(=O)[C@@H](NC(C)=O)C(C)(C)C)C(=O)C(=O)NC1CC1] Jun9-66-3 | 1.52 |

TABLE 5-continued
| Structure | SARS-CoV-2 Mpro inhibition IC50 (μM) |
|---|---|
| 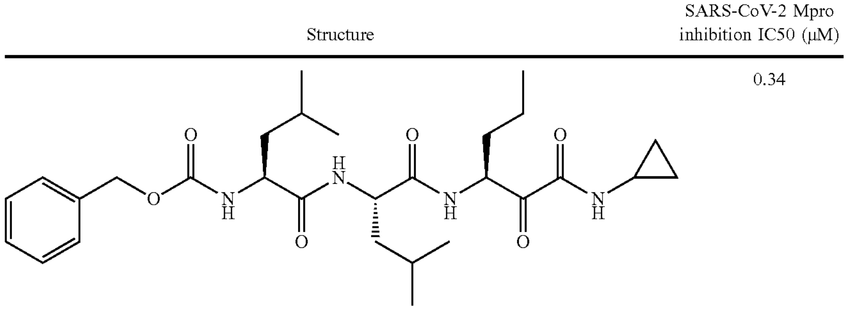 Jun8-18-4 | 0.34 |
| 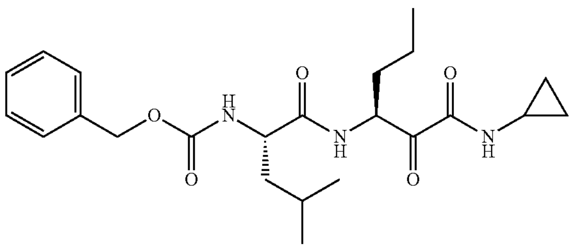 [SMILES: CCC[C@H](NC(=O)[C@H](CC(C)C)NC(=O)OCc1ccccc1)C(=O)C(=O)NC1CC1] Jun8-18-2 | >20 |
| 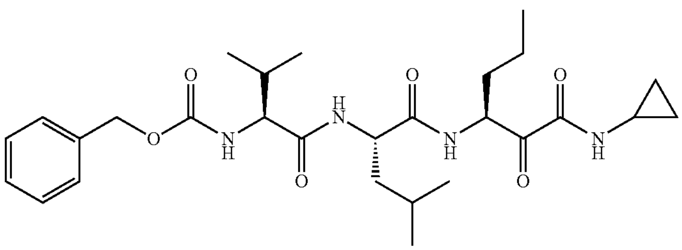 [SMILES: CCC[C@H](NC(=O)[C@H](CC(C)C)NC(=O)[C@@H](NC(=O)OCc1ccccc1)C(C)C)C(=O)C(=O)NC1CC1] Jun8-29-2 | 0.48 |
| 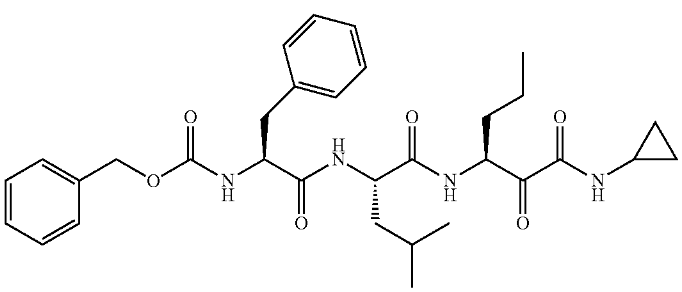 [SMILES: CCC[C@H](NC(=O)[C@H](CC(C)C)NC(=O)[C@H](Cc1ccccc1)NC(=O)OCc1ccccc1)C(=O)C(=O)NC1CC1] Jun8-29-4 | 0.48 |
| 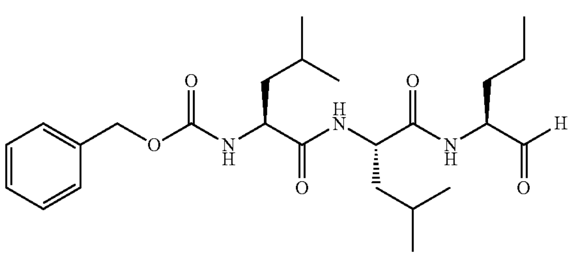 [SMILES: CCC[C@@H](C=O)NC(=O)[C@H](CC(C)C)NC(=O)[C@H](CC(C)C)NC(=O)OCc1ccccc1] Jun9-48-2 | 1.49 |

TABLE 5-continued
| Structure | SARS-CoV-2 Mpro inhibition IC50 (μM) |
| --- | --- |
| 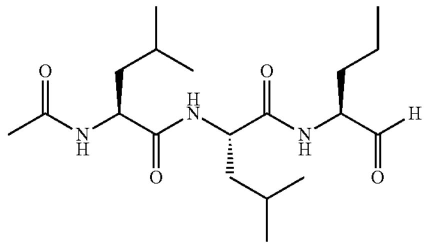 [SMILES: CCC[C@@H](C=O)NC(=O)[C@H](CC(C)C)NC(=O)[C@H](CC(C)C)NC(C)=O] Jun9-48-3 | 38.5 |
| 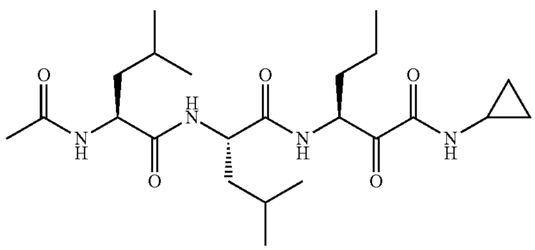 [SMILES: CCC[C@H](NC(=O)[C@H](CC(C)C)NC(=O)[C@H](CC(C)C)NC(C)=O)C(=O)C(=O)NC1CC1] Jun9-49-1 | 5.89 |
| 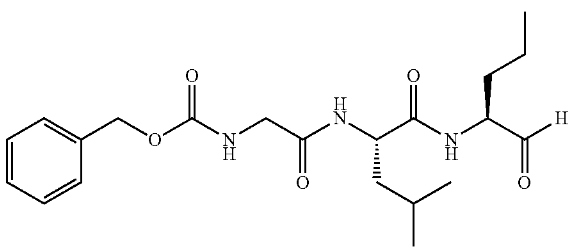 [SMILES: CCC[C@@H](C=O)NC(=O)[C@H](CC(C)C)NC(=O)CNC(=O)OCc1ccccc1] Jun9-52-3 | >20 |
| 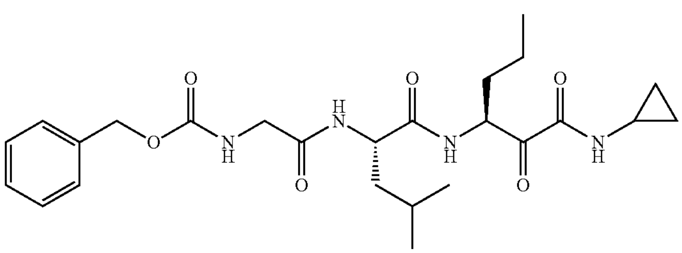 [SMILES: CCC[C@H](NC(=O)[C@H](CC(C)C)NC(=O)CNC(=O)OCc1ccccc1)C(=O)C(=O)NC1CC1] Jun9-52-4 | 17.7 |
| 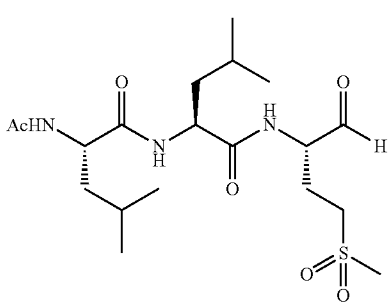 [SMILES: CC(=O)N[C@@H](CC(C)C)C(=O)N[C@@H](CC(C)C)C(=O)N[C@H](C=O)CCS(C)(=O)=O] Jun9-58-1 | 0.49 |

TABLE 5-continued
| Structure | SARS-CoV-2 Mpro inhibition IC50 (μM) |
|---|---|
| 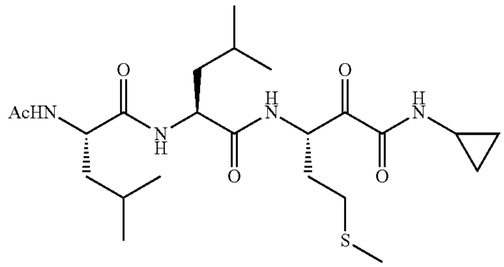 [SMILES: CSCC[C@H](NC(=O)[C@H](CC(C)C)NC(=O)[C@H](CC(C)C)NC(C)=O)C(=O)C(=O)NC1CC1] Jun9-11-3 | 0.54 |
| 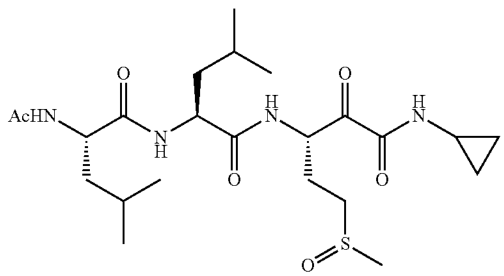 [SMILES: CC(=O)N[C@@H](CC(C)C)C(=O)N[C@@H](CC(C)C)C(=O)N[C@@H](CCS(C)=O)C(=O)C(=O)NC1CC1] Jun9-59-2 | 0.36 |
| 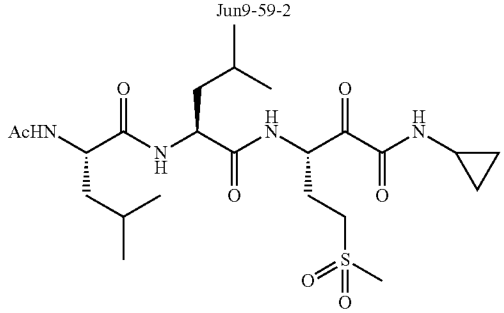 Jun9-65-1 | 0.18 |
| 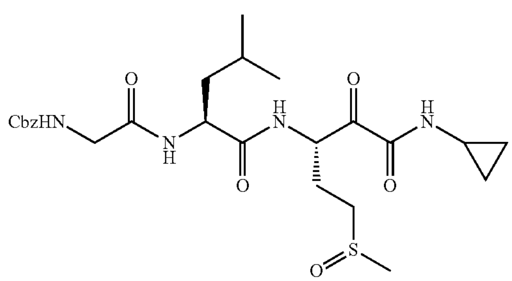 [SMILES: CC(C)C[C@H](NC(=O)CNC(=O)OCc1ccccc1)C(=O)N[C@@H](CCS(C)=O)C(=O)C(=O)NC1CC1] Jun9-24-1 | 0.51 |
| 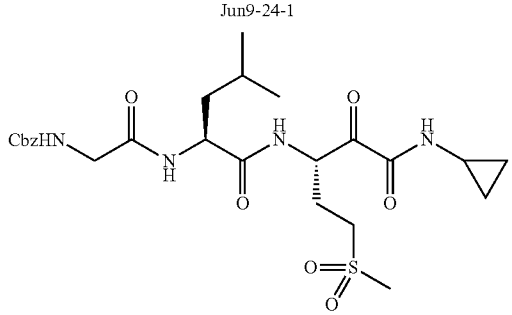 Jun9-56-2 | 0.13 |

TABLE 5-continued

| Structure | SARS-CoV-2 Mpro inhibition IC50 (μM) |
| --- | --- |
| 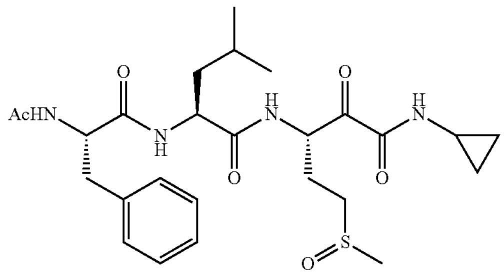 [SMILES: CC(=O)N[C@@H](Cc1ccccc1)C(=O)N[C@@H](CC(C)C)C(=O)N[C@@H](CCS(C)=O)C(=O)C(=O)NC1CC1] Jun9-24-4 | 0.29 |
| 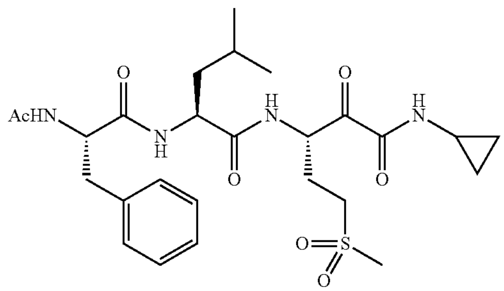 [SMILES: CC(=O)N[C@@H](Cc1ccccc1)C(=O)N[C@@H](CC(C)C)C(=O)N[C@@H](CCS(C)(=O)=O)C(=O)C(=O)NC1CC1] Jun9-56-3 | 0.14 |
| 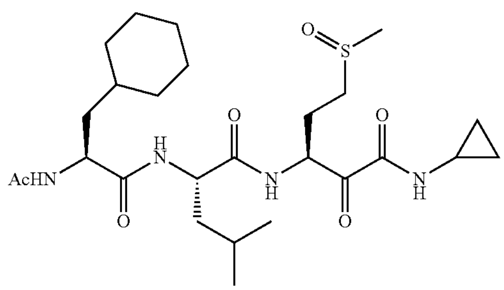 [SMILES: CC(=O)N[C@@H](CC1CCCCC1)C(=O)N[C@@H](CC(C)C)C(=O)N[C@@H](CCS(C)=O)C(=O)C(=O)NC1CC1] Jun9-87-4 | 0.27 |
| 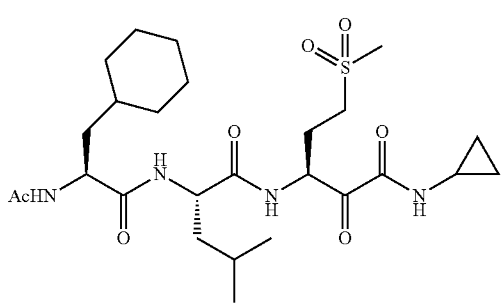 [SMILES: CC(=O)N[C@@H](CC1CCCCC1)C(=O)N[C@@H](CC(C)C)C(=O)N[C@@H](CCS(C)(=O)=O)C(=O)C(=O)NC1CC1] Jun9-82-2 | 0.10 |

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes.

What is claimed is:
1. A compound encompassed within Formulas I:
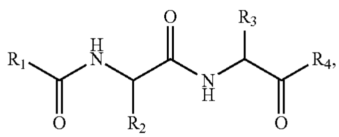
including pharmaceutically acceptable salts, solvates, and/or prodrugs thereof,
wherein R1 is selected from the group consisting of hydrogen, methyl,
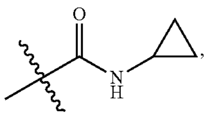
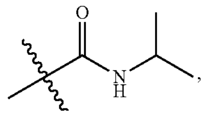
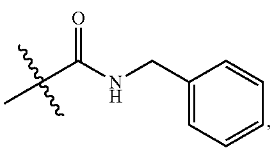
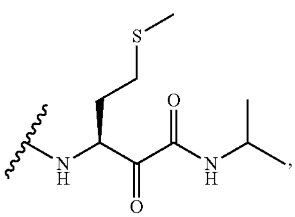
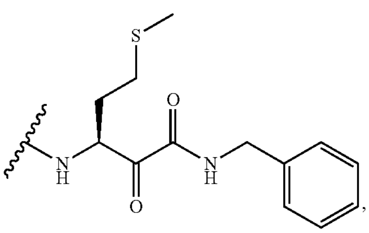
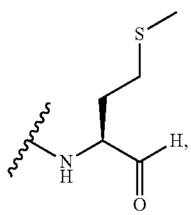
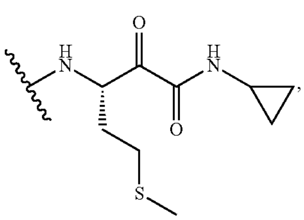
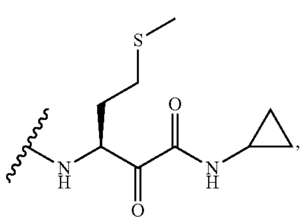
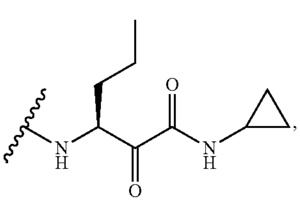
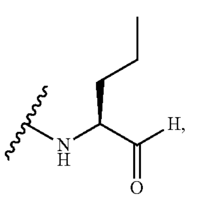
-continued
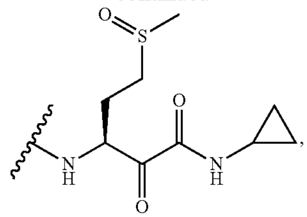
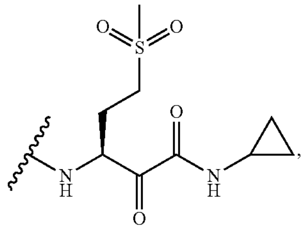
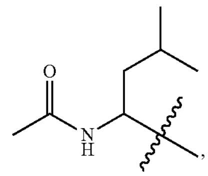
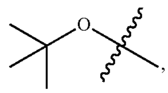
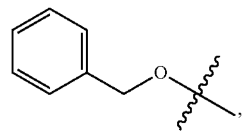
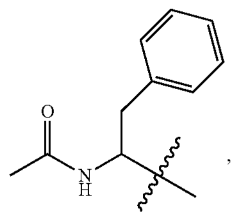
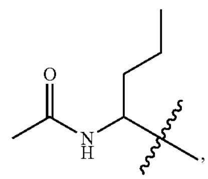
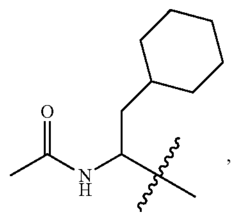
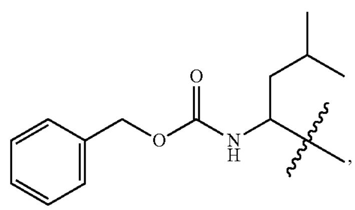
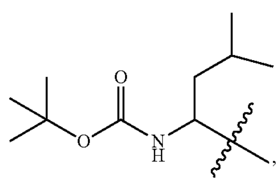
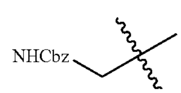
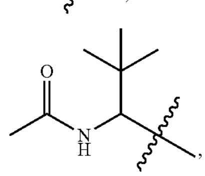
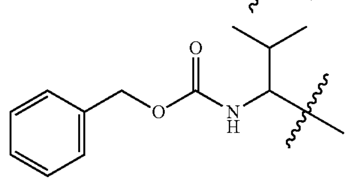
and

-continued
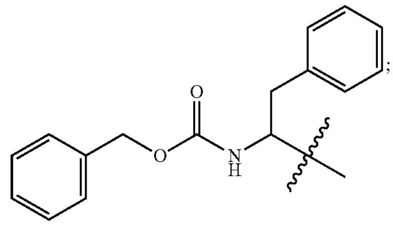;
wherein R2 is selected from the group consisting of hydrogen,
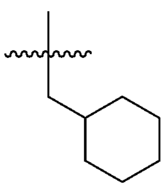, 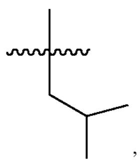 [SMILES: *CC(C)C], 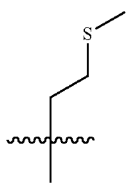,
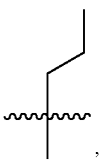, 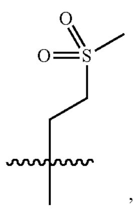, 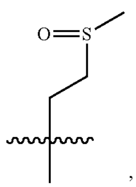, 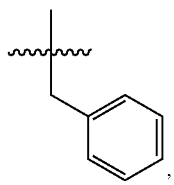,
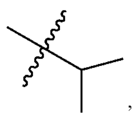, and 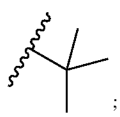;
wherein R3 is selected from the group consisting of hydrogen,
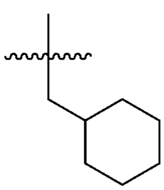, 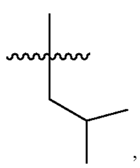, 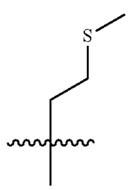,
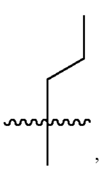, 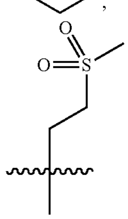, 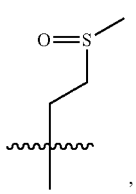, 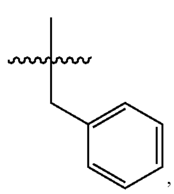,
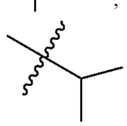, and 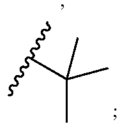;
wherein R4 is selected from the group consisting of hydrogen, methyl,
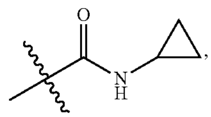, 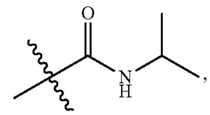,
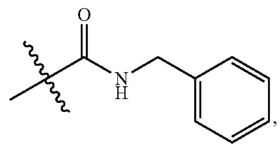, 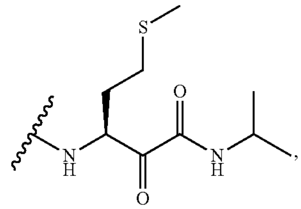,
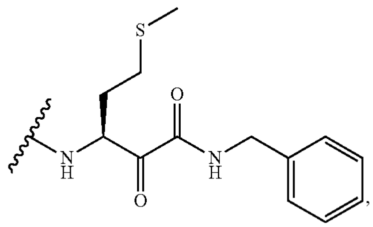, 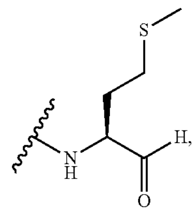
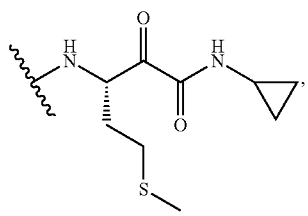,
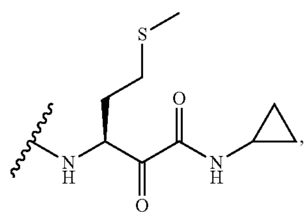,
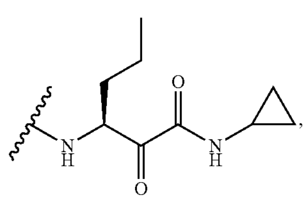, 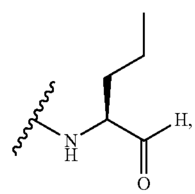
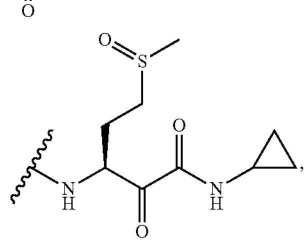,
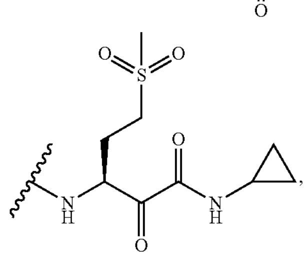, 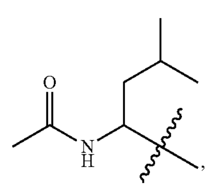, -continued
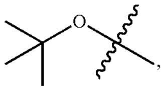,
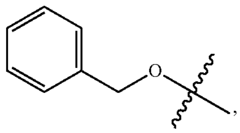,
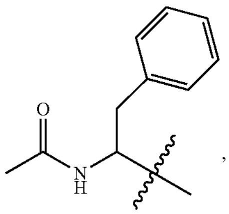,
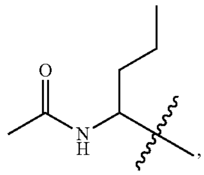,
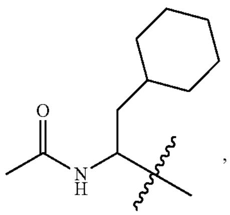,
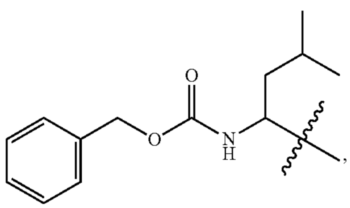,
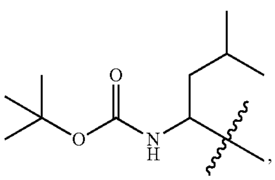,
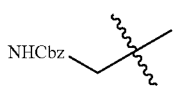,
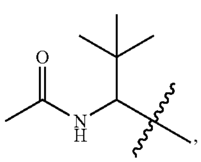,
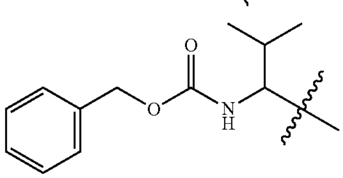, and
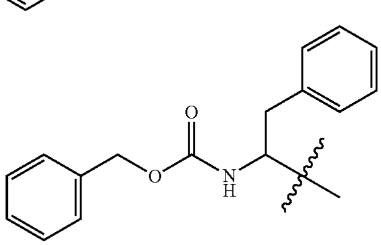;
wherein if R1 is methyl, R2 is
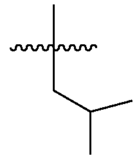,
and R3 is
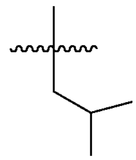,
then R4 cannot be
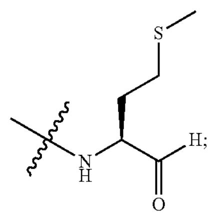
wherein if R4 is methyl, R2 is
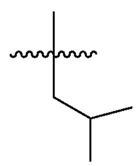,
and R3 is
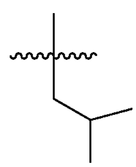,
then R1 cannot be
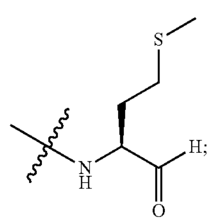

Wherein if R4 is

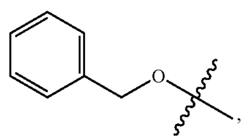 [SMILES: *OCc1ccccc1]

then R1 cannot be

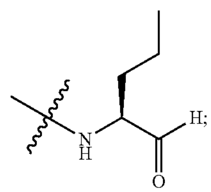

Wherein if R1 is

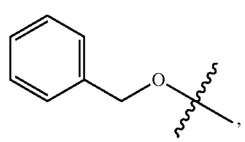 [SMILES: *OCc1ccccc1]

then R4 cannot be

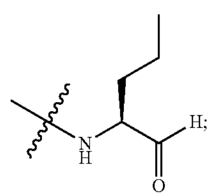

2. The compound of claim 1, wherein the compound is capable of inhibiting $M^{pro}$ protease activity; and/or wherein the compound is capable of treating, ameliorating, and/or preventing viral infection (e.g., COVID-19 infection).

3. The compound of claim 1, wherein said compound is selected from the group consisting of:

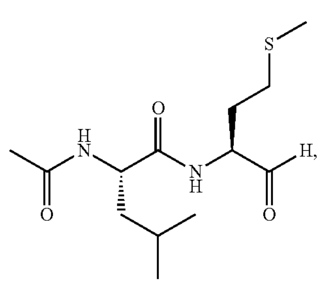

-continued

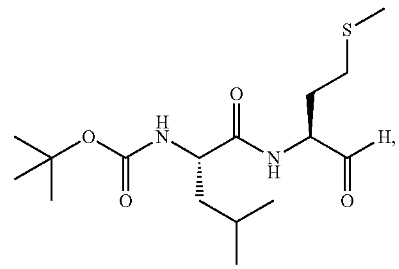

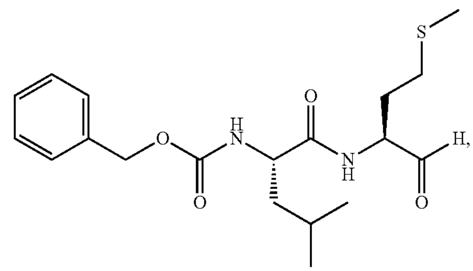

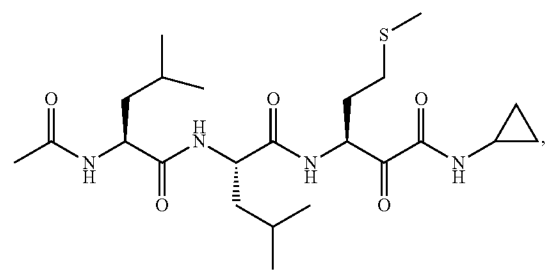

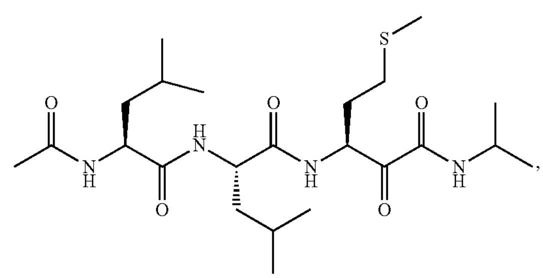

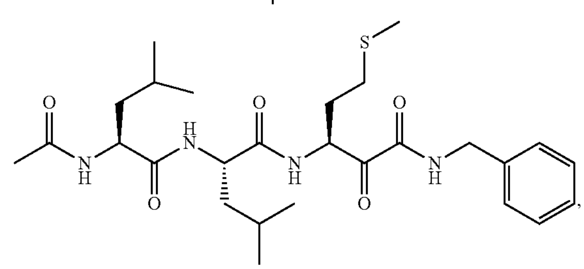

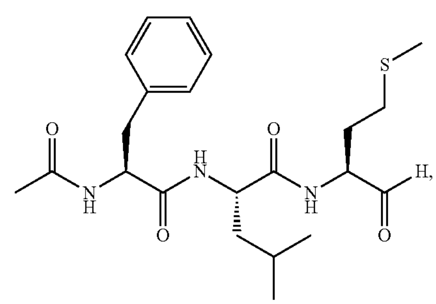

-continued
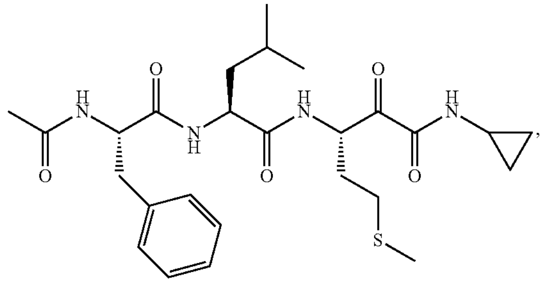
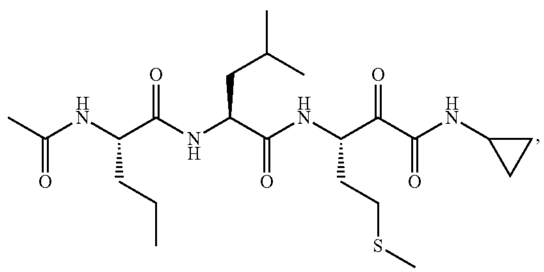
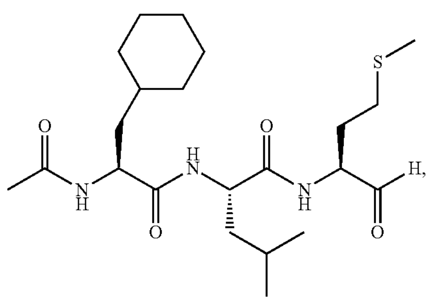
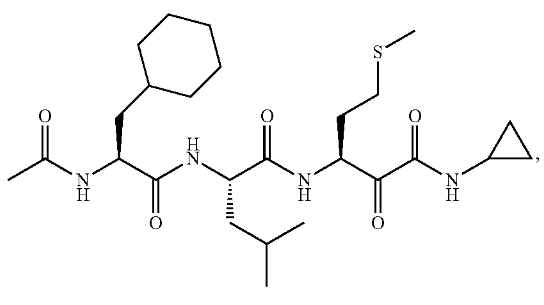
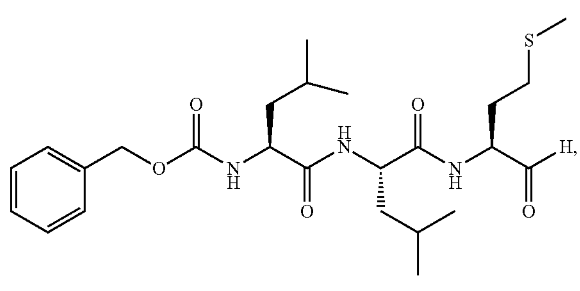
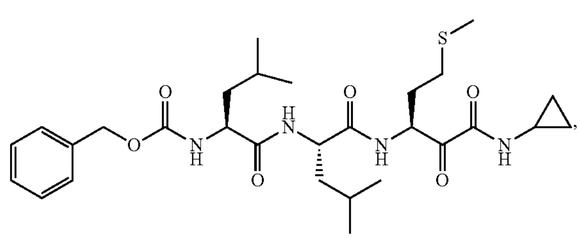
-continued
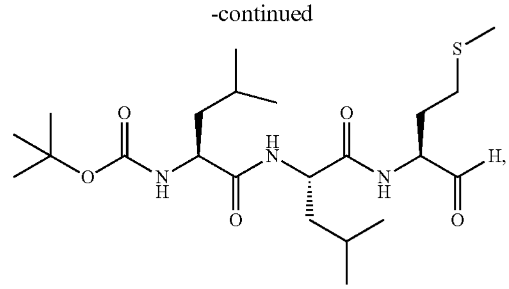
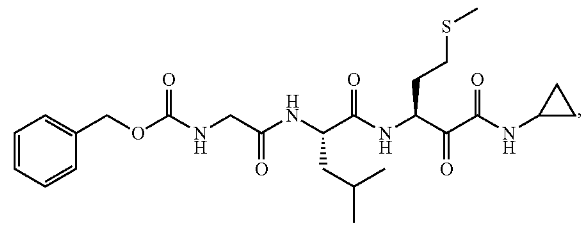
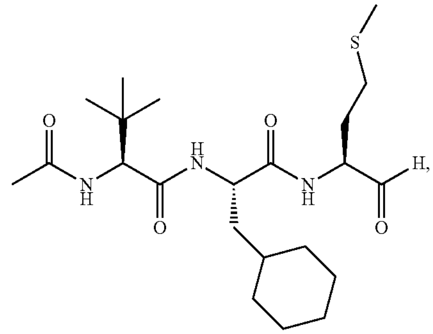
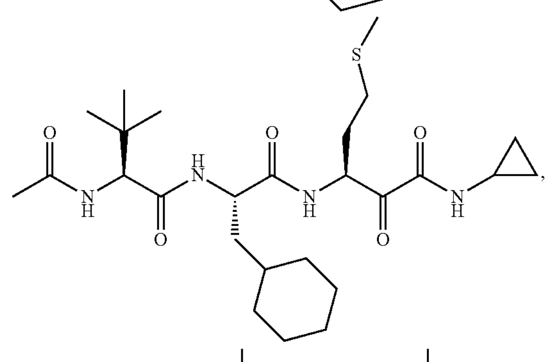
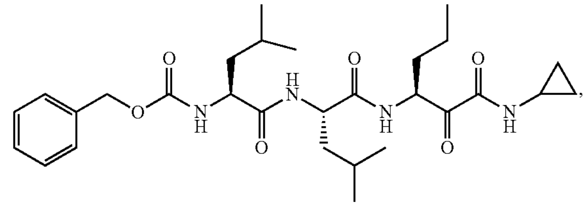
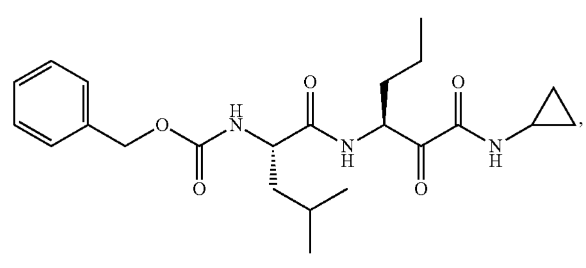

-continued
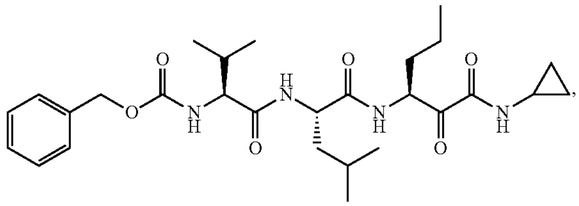,
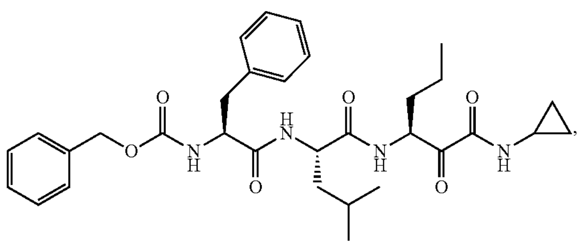,
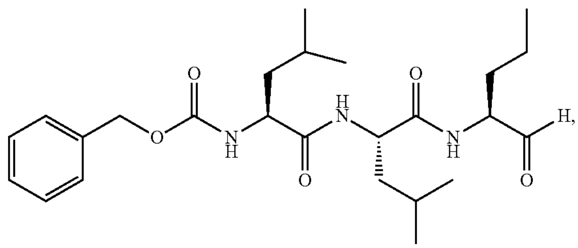,
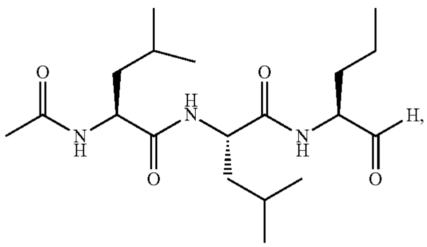,
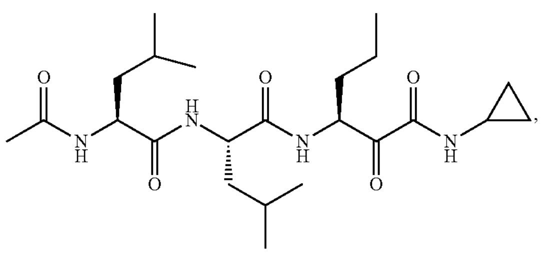,
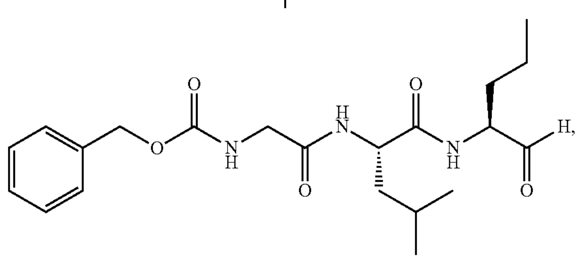,
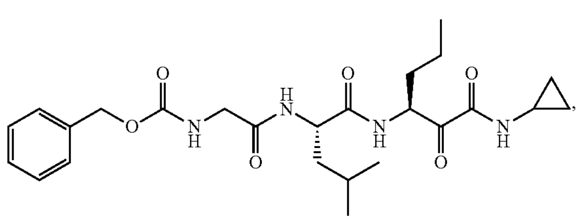,
-continued
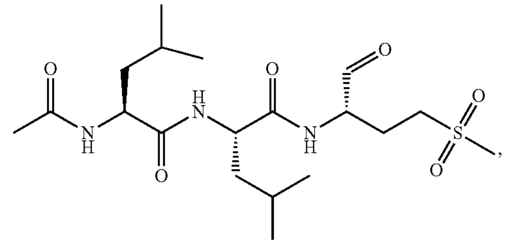,
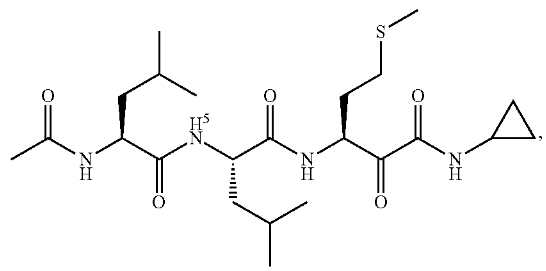,
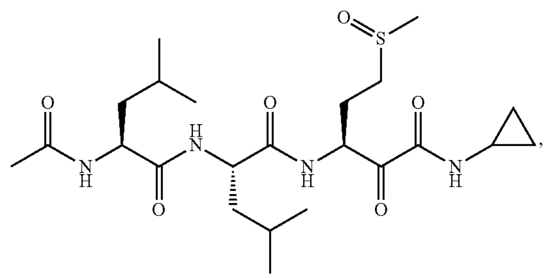,
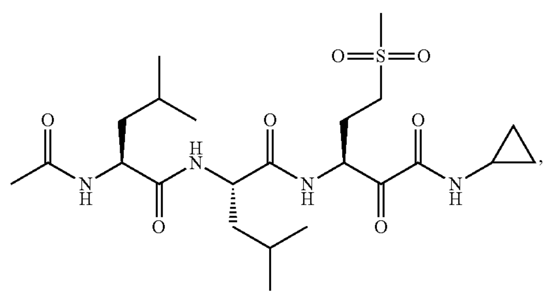,
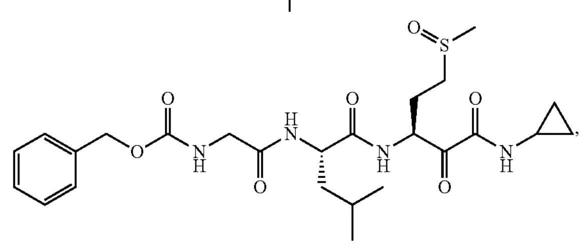,
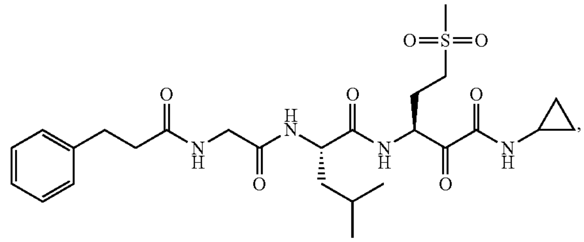, -continued

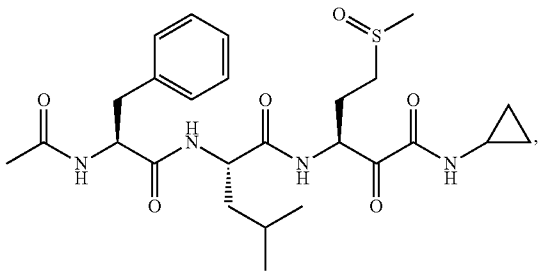

,

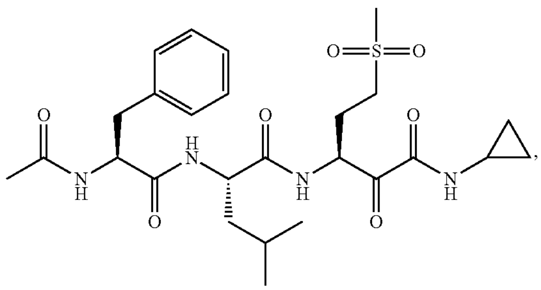

,

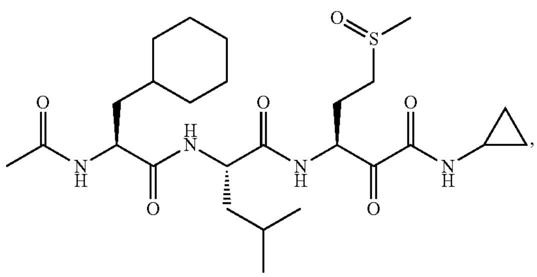

, and

-continued

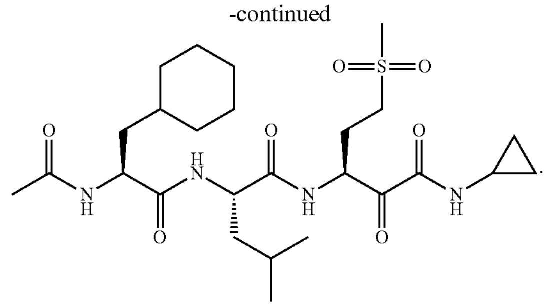

.

4. A pharmaceutical composition comprising a compound of claim 1.

5. A method for treating, or ameliorating SARS-COV-2 infection in a subject, comprising administering to the subject a therapeutically effective amount of the pharmaceutical composition of claim 4.

6. The method of claim 5, wherein the pharmaceutical composition is dispersed in a pharmaceutically acceptable carrier.

7. The method of claim 5, wherein the administering results in suppression of $M^{pro}$ activity.

8. The method of claim 5, wherein the administering is oral, topical or intravenous.

9. The method of claim 5, further comprising administering to the subject one or more of hydroxychloroquine, dexamethasone, and remdesivir.

10. The method of claim 5, wherein the symptoms related to viral infection in a subject are one or more of fever, fatigue, dry cough, myalgias, dyspnea, acute respiratory distress syndrome, and pneumonia.

* * * * *